(12) United States Patent
Čopar et al.

(10) Patent No.: US 6,489,318 B1
(45) Date of Patent: Dec. 3, 2002

(54) ETHYLIDENE DERIVATIVES OF TRICYCLIC CARBAPENEMS

(75) Inventors: Anton Čopar, Šmartho Pri Litiji (SI); Tomaž Šolmajer, Ljubljana (SI); Borut Anžič, Trzin (SI); Tadeja Kuzman, Lujubljana (SI); Tomaž Mesar, Trizin (SI); Darko Kocjan, Ljubljana (SI)

(73) Assignee: LEK, tovarna farmacevtskih in kemicnih izdelkov, d.d., Ljubljana (SI)

( * ) Notice: Subject to any disclaimer, the term of this patent is extended or adjusted under 35 U.S.C. 154(b) by 0 days.

(21) Appl. No.: 09/319,660

(22) PCT Filed: Dec. 18, 1997

(86) PCT No.: PCT/SI97/00035

§ 371 (c)(1),
(2), (4) Date: Jun. 10, 1999

(87) PCT Pub. No.: WO98/27094

PCT Pub. Date: Jun. 25, 1998

(30) Foreign Application Priority Data

Dec. 18, 1996 (SI) ............................................. P-9600371

(51) Int. Cl.$^7$ .................... C07D 477/14; A61K 31/407; A61P 31/04
(52) U.S. Cl. ................... 514/210.03; 540/302
(58) Field of Search ....................... 540/302; 514/210.03

(56) References Cited

U.S. PATENT DOCUMENTS

| | | | | |
|---|---|---|---|---|
| 4,235,922 A | 11/1980 | Ratcliffe et al. | ............ | 514/210 |
| 5,459,260 A | 10/1995 | Sendai et al. | ............... | 540/302 |

FOREIGN PATENT DOCUMENTS

| | | |
|---|---|---|
| EP | 0 005 349 | 11/1979 |
| EP | 0 422 596 | 10/1990 |
| EP | 0 502 464 | 9/1992 |
| EP | 0 502 465 | 9/1992 |
| WO | WO 95/13278 | 5/1995 |
| WO | WO 95/23149 | 8/1995 |

OTHER PUBLICATIONS

Di Fabio, R., et al., "Synthesis and Biological Evaluatoin of 4–Heterotribactams," *Bioorganic & Medical Chemistry Letters*, vol. 5, No. 12, pp. 1235–1240, 1995.
Ghiron, C., et al., "The Stereoselective Synthesis of a Key Intermediate of the Trinem Antiboitic Sanfetrinem," *Tetrahedron Letters*, vol. 17, No. 22, pp. 3891–3894, 1996.
Abstract for JP 5–021232 (6/94.

*Primary Examiner*—Mark L. Berch
(74) *Attorney, Agent, or Firm*—Connolly Bove Lodge & Hutz, LLP

(57) ABSTRACT

Disclosed are novel ethylidene derivatives of tricyclic carbapenems of the formula I

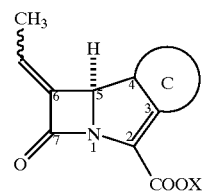

wherein the ring marked C and X have the meaning as in the description, in the form of pure diastereoisomers and in the form of pure geometric isomers. Novel ethylidene derivatives of tricyclic carbapenems of the formula I are used as inhibitors of the action of the enzyme β-lactamase and/or as antibiotics in human and veterinary medicine. Also disclosed are pharmaceutical formulations for the treatment of bacterial infections of human and animal organisms comprising as an active ingredient a therapeutically effective amount of an ethylidene derivative of tricyclic carbapenems of the formula I in the form of an acid, a pharmaceutically acceptable salt or ester thereof and optionally in a combination with a β-lactam antibiotic, and usual pharmaceutically acceptable carriers and auxiliary substances.

Also disclosed is a process for the preparation of novel ethylidene derivatives of tricyclic carbapenems of the formula I.

17 Claims, No Drawings

ETHYLIDENE DERIVATIVES OF TRICYCLIC CARBAPENEMS

RELATED APPLICATION

This application is a national phase application under 35 U.S.C. §371 of International Application No. PCT/SI97/00035, Dec. 18, 1997.

TECHNICAL FIELD +ps (C07D 477/00, A61K 31/40)

The invention belongs to the field of pharmaceutical industry and relates to novel ethylidene derivatives of tricyclic carbapenems in the form of pure diastereoisomers and in the form of pure geometric isomers, to processes for the preparation thereof, to pharmaceutical compositions containing them and to the use thereof in human and veterinary medicine. Novel ethylidene derivatives of tricyclic carbapenems are used as inhibitors of action of β-lactamases and/or as antibiotics.

Technical Problem

Due to the phenomenon of resistance to various antibiotics and synthetic chemotherapeutics, there exists a constant need to prepare novel effective antiinfection agents. There also exists a constant need to prepare novel inhibitors of enzymes β-lactamases which are responsible for the resistance against β-lactam antibiotics. Novel ethylidene derivatives of tricyclic carbapenems are chemical compounds which are inhibitors of enzymes β-lactamases and/or antibiotics.

Prior Art

In prior art carbapenem compounds are known as effective antibacterial agents. A novel sub-group of carbapenem compounds are tricyclic carbapenems (first disclosed in EP-A-416953 and EP-A-422596) which are novel antibacterial agents in a broad spectrum of pathogenic gram-negative and gram-positive bacteria as inhibitors of the enzyme D,D-peptidase (A. Perboni et al. in Recent Advances in the Chemistry of Antiinfective Agents, Bentley, H. H., Ponsford, R. Eds., The Royal Society of Chemistry, T. Graham House, Cambridge, 1992, p. 21 and S. Hannesian et al., Bioorg. Med. Chem. Lett. 5, (1995) 2535).

Tricyclic carbapenem compounds with an antibacterial action are also disclosed in U.S. Pat. No. 5,459,260, EP-A-502464, EP-A-502465, EP-A-502468, EP-A-517065, PCT-WO-94/05666, U.S. Pat. Nos. 5,372,993, 5,374,630, PCT-WO-94/21637, PCT-WO-94/21638, PCT-WO-95/03700, PCT-WO-95/13278, PCT-WO-95/23149, JP 06,166688 and JP 08,53459.

The compound 4S,8S-4methoxy-(9R)10S,12R)-10-(1-hydroxyethyl)-11-oxo-1-azatricyclo-[7.2.0.0$^{3.8}$]undec-2-ene (GV104326 or sanfetrinem) is a biologically active molecule with an action on the enzyme D,D-peptidase which is essential for the formation of the cell wall in the process of bacterial multiplication (E. di Mvodugno et al., Antimicrob. Agents Chemother. 38 (1994) 2362).

Bycyclic carbapenem compounds with an antibacterial action are described in EP-A-0005349 and U.S. Pat. No. 4,235,922. There are no data about said compounds being inhibitors of enzyme β-lactamase.

In all hitherto disclosed tricyclic carbapenem compounds there are no data on any inhibition action to enzymes of the β-lactamase species. Thus, the object of the present invention are novel ethylidene derivatives of tricyclic carbapenem compounds with a completely novel structure and with the property of inhibiting the enzyme β-lactamase. This property does not reduce the possibility of potential antibacterial activity thereof.

The Technical Solution

The invention relates to novel ethylidene derivatives of tricyclic carbapenems of the formula I

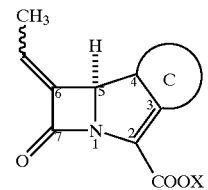

wherein the ring marked C fused to the basic carbapenem nucleus in 3and 4 positions is a five-, six- or seven-membered ring whereat 1. one or more carbon atoms in the ring marked C may be mono or disubstituted with substituents which may be the same or different and may mean:
   a) a hydrogen atom.
   b) a saturated alkyl chain with 1 to 20 carbon atoms and the saturated alkyl chain may be straight (such as methyl, ethyl, n-propyl, n-butyl) or branched in any position (such as isopropyl, s-butyl, isobutyl, isoamyl, tert-butyl) and each chain member may be mono or disubstituted with substituents such as halo (such as fluoromethyl, trifluoromethyl, 2-chloroethyl), hydroxy (such as hydroxymethyl, 2-hydroxyethyl), ($C_1$–$C_4$)-alkyloxy (such as methoxymethyl, 2-methoxyethyl), mercapto and ($C_1$–$C_4$)-alkylmercapto (such as mercaptomethyl, 2-methylmercaptoethyl), ($C_1$–$C_4$)-alkanesulfonyl (such as methanesulfonylmethyl), amino, ($C_1$–$C_4$)-alkylamino and di-($C_1$–$C_4$)-alkylamino (such as 2-aminoethyl, 2-methylaminoethyl, 2-dimethylaminoethyl), alkyleneamino (such as 2-(1-piperidinyl)ethyl, 1-pyrrolidinylmethyl), guanidino (such as guanidinomethyl), unsubstituted $N^1$-mono, $N^3$-mono, $N^1,N^3$-di and $N^3,N^3$-di-($C_1$–$C_4$)-formamidino (such as iminomethylaminomethyl, 2-(dimethylaminomethyleneamino)ethyl), aromatic or heteroaromatic five- or six-membered ring (such as phenyl, furyl, 2-pyridyl), ($C_1$–$C_4$)-alkyloxycarbonyl (such as carbethoxymethyl), cyano (such as 2-cyanoethyl), oxo (such as acetyl, propionyl, 2-oxopropyl),
   c) an unsaturated alkyl chain with 1 to 20 carbon atoms and the unsaturated alkyl chain may be straight with double bonds or triple bonds (such as vinyl, propenyl, allyl, ethinyl, propargyl) or branched in any position with double bonds or triple bonds (such as 2-propenyl) and each chain member may be mono or disubstituted with substituents such as halo, hydroxy, ($C_1$–$C_4$)-alkyloxy, thio and ($C_1$–$C_4$)-alkylthio, ($C_1$–$C_4$)-alkanesulfonyl, amino, ($C_1$–$C_4$)-alkylamino and di-($C_1$–$C_4$)-alkylamino, aromatic or heteroaromatic five- or six-membered ring (such as phenyl, furyl, 2-pyridyl), ($C_1$–$C_4$)-alkyloxycarbonyl, cyano, oxo,
   d) a saturated or partly unsaturated cycloalkyl radical with 3 to 7 members (such as radicals from cyclopropyl to cycloheptyl, cyclohex-1-enyl) and the ring may comprise one or more oxygen, sulfur or nitrogen atoms (such as 2-tetrahydrofuranyl, 1-piperidinyl, 1-pyrrolidinyl) and each ring member may be mono or disubstituted with substituents such as halo, hydroxy, $(C_1-C_4)$-alkyloxy, thio and $(C_1-C_4)$-alkylthio), $(C_1-C_4)$-alkanesulfonyl, amino, $(C_1-C_4)$-alkylamino and di-$(C_1-C_4)$-alkylamino, $(C_1-C_4)$-alkyloxycarbonyl, cyano, oxo, e) an aromatic or heteroaromatic five- or six-membered ring (such as phenyl, furyl, 2-pyridyl), f) a hydroxy, $C_1-C_{10}$)-alkyloxy (such as methoxy, ethoxy, n-propoxy, isopropoxy, tert-butoxy, cyclohexyloxy), mono or disubstituted $(C_1-C_{10})$-alkyloxy (such as 2-hydroxyethyloxy), 2,3-dihydroxyprop-1-yloxy, 2-methoxyethyloxy, fluoromethyloxy, aminoethyloxy, 2-dimethylaminoethyloxy), acyloxy (such as formyloxy, acetyloxy, benzoyloxy, ethoxycarbonyloxy, allyloxycarbonyloxy), mono, di or tri-$(C_1-C_4)$-alkylsilyloxy (such as trimethylsilyloxy, tert-butyldimethylsilyloxy) group, g) a mercapto, $(C_1-C_{10})$-alkylmercapto (such as methylmercapto, ethylmercapto), mono or disubstituted $(C_1-C_{10})$-alkylmercapto (such as 2-hydroxyethylmercapto, 2,3-dihydroxyprop-1-ylmercapto, 2-methoxyethylmercapto, 2-mercaptoethylmercapto, 2-methylmercaptoethylmercapto, 2-aminoethylmercapto, 2-dimethylaminoethylmercapto), acylmercapto (such as acetylmercapto) group, h) an amino, $(C_1-C_4)$-alkylamino and di-$(C_1-C_4)$-alkylamino (such as methylamino, dimethylamino, 2-hydroxyethylamino, bis(2-hydroxyethyl)amino, aminoethyloxy, 2-dimethylaminoethyloxy, 2-aminoethylamino, 2-piperidinoethylamino), acetylamino, allyloxycarbonylamino, iminomethylamino, N-methylaminomethyleneamino, N,N-dimethylaminomethyleneamino, guanidino, cyanoguanidino, methylguanidino group, i) a halo atom (such as fluoro, chloro, bromo, iodo), j) an azido, nitro, cyano, $(C_1-C_4)$-alkyloxycarbonyl (such as carbomethoxy, carbethoxy) group, k) a $(C_1-C_4)$-alkanesulfonyl group (such as methanesulfonyl, ethanesulfonyl);

2. one or more carbon atoms in the ring marked C may be substituted with a substituted or unsubstituted alkyl chain which is linked to the ring marked C via double bond in the form of >C*=CR¹R², and C* means a carbon atom in the ring marked C,=means an exocyclic double bond and the substituents R¹ and R², which may be the same or different, may mean:

a) a hydrogen atom so that the substituent is methylene, b) an unsubstituted saturated alkyl chain with 1 to 20 carbon atoms and the unsubstituted saturated alkyl chain may be straight (such as ethylidene, n-propylidene, n-butylidene, isopropylidene) or branched in any position (such as 2,2-dimethylpropylidene), c) an unsubstituted unsaturated alkyl chain with 1 to 20 carbon atoms and the unsubstituted unsaturated alkyl chain may be straight or branched with double bonds or triple bonds (such as vinylidene, allylidene), d) an unsubstituted saturated or partly unsaturated cycloalkyl or heteroaryl with 3 to 7 members (as comprised in groups from cyclopropylmethylene to cycloheptylmethylene), e) an aromatic or heteroaromatic five- or six-membered ring (as comprised in groups such as benzylidene, diphenylmethylene), f) a substituted saturated or partly unsaturated alkyl chain or substituted three- to seven-membered carbocyclic ring whereat any carbon atom in the chain or in the ring may be mono or disubstituted with substituents such as halo, hydroxy, $(C_1-C_4)$-alkyloxy, $(C_1-C_4)$-alkylthio, $(C_1-C_4)$-alkanesulfonyl, amino, $(C_1-C_4)$-alkylamino, di-$(C_1-C_4)$-alkylamino, $(C_1-C_4)$-alkyloxycarbonyl, cyano, oxo as comprised in groups such as hydroxyethylidene, methoxyethylidene, g) a hydroxy, $(C_1-C_4)$-alkyloxy, acyloxy, mercapto, $(C_1-C_4)$-alkylmercapto, amino, $(C_1-C_4)$-alkylamino, di-$(C_1-C_4)$-alkylamino and acylamino group as comprised in groups such as hydroxymethylene, methoxymethylene, dimethoxymethylene, dimethylaminomethylene, acetylaminomethylene groups, h) a nitro, cyano, $(C_1-C_4)$-alkyloxycarbonyl group so that the substituent is dicyanomethylene, bis(carbomethoxy)methylene, carbethoxymethylene;

and the substituents R¹ and R² may also mean a joint alkylene chain $(CH_2)_n$ (n=2 to 7) closed to a ring and any methylene (—CH₂—) member may be replaced by oxa (—O—), thia (—S—), imino (—NH—) or $(C_1-C_4)$-alkylimino group as comprised in groups such as cyclopentylidene, cyclohexylidene, 2-(1,3-dioxacyclopentylidene);

3. one or more carbon atoms in the ring marked C may be substituted with a hetero atom via double bond (such as oxo, thioxo, hydroxyimino, $(C_1-C_4)$-alkylimino, acylimino);

4. one or more carbon atoms in the ring marked C may be disubstituted with substituents closed to a ring to obtain a spiro compound and, besides a carbon atom, the ring members may also be oxygen, sulfur and nitrogen atoms (such as ethylene, 1,3-propylene, 1,5-pentylene, ethylenedioxy);

5. one or more carbon atoms in the ring marked C may be replaced by an oxygen atom;

6. one or more carbon atoms in the ring marked C may be replaced with a sulfur atom which may be mono or dioxidized to obtain sulfoxides or sulfones;

7. one or more carbon atoms in the ring marked C may be replaced with a nitrogen atom which may be substituted in the form of >N*-R³ and N* means a nitrogen atom in the ring marked C and R³ may mean:

a) a saturated alkyl chain with 1 to 20 carbon atoms and the unsubstituted saturated chain may be straight (such as methyl, ethyl, n-propyl, n-butyl) or branched in any position (such as isopropyl, s-butyl, isobutyl, isoamyl, tert-butyl) and each chain member may be once or several times substituted with substituents such as halo (such as fluoromethyl, trifluoromethyl, 2-chloroethyl), hydroxy (such as 2-hydroxyethyl), $(C_1-C_4)$-alkyloxy (such as 2-methoxyethyl), $(C_1-C_4)$-alkylthio (such as methylmercaptoethyl), $(C_1-C_4)$-alkanesulfonyl (such as methanesulfonylmethyl), amino, $(C_1-C_4)$-alkylamino, di-$(C_1-C_4)$-alkylamino (such as 2-aminoethyl, 2-methylaminoethyl, 2-dimethylaminoethyl), aromatic or heteroaromatic five- or six-membered ring (such as phenyl, furyl, 2-pyridyl), ($C_1$–$C_4$)-alkyloxycarbonyl (such as carbethoxymethyl), cyano (such as cyanoethyl), oxo (such as acetyl, propionyl, 2-oxopropyl), imino (such as iminomethyl, aminoiminomethyl, aminocyanoiminomethyl), b) an unsubstituted unsaturated alkyl chain with 1 to 20 carbon atoms and this unsubstituted unsaturated alkyl chain may be straight with double bonds (such as vinyl, propenyl, allyl) or triple bonds (such as ethinyl, propargyl) or branched in any position with double or triple bonds (such as 2-propenyl), c) an unsubstituted saturated or partly unsaturated cycloalkyl or heteroaryl radical with 3 to 7 members (such as radicals from cyclopropyl to cycloheptyl, cyclohex-1-enyl, 4-piperidinyl), d) an unsubstituted aromatic or heteroaromatic five- or six-membered ring (such as phenyl, furyl, 2-pyridyl), e) groups such as cyano, ($C_1$–$C_4$)-alkyloxycarbonyl (such as carbomethoxy, carboethoxy), aminocarbonyl, ($C_1$–$C_4$)-alkylaminocarbonyl, ($C_1$–$C_4$)-alkylsulfonyl (methanesulfonyl);

and wherein X may mean:

1. a hydrogen atom so that the compound of the formula I is a carboxylic acid; in the case of a basic centre in the molecule, a hydrogen atom is linked to it as a proton, the carboxyl group is in the anion form as carboxylate and the compound of the formula I is in the form of a zwitter ion, 2. an alkali metal so that the compound of the formula I is an alkali metal salt (such as lithium carboxylate, sodium carboxylate, potassium carboxylate), 3. an earth alkali metal so that the compound of the formula I is an earth alkali metal salt wherein for one bivalent metal ion there are two carboxylate anions (such as calcium dicarboxylate), 4. the ammonium ion or a protonated form of mono, di or trisubstituted acyclic or cyclic aliphatic amine or a protonated form of some other nitrogen base. The compound of the formula I is in this case a salt of a carboxylic acid and ammonia or amine (such as trimethylamine, triethylamine, N,N'-dibenzylethylenediamine, ethanolamine, diethanolamine, triethanolamine, dicyclohexylamine, 2-piperidinyl) or amidine (such as 1,8-diazabicyclo[5.4.0]undec-7-ene, 1,5-diazabicyclo[4.3.0]non-5-ene, 3,3,6,9,9-pentadimethyl-2,10-diaza-bicyclo[4.4.0]dec-1-ene) or guanidine (such as guanidine, cyanoguanidine) or some other nitrogen base (such as 4-dimethylaminopyridine, imidazole), 5. the quaternized ammonium ion so that the compound of the formula I is a corresponding quaternary ammonium carboxylate (such as tetrabutylammonium carboxylate), 6. a radical $R^4$ whereat the compound of the formula I is in the ester form and the radical $R^4$ may be:

a) selected from the group comprising ($C_1$–$C_{20}$)-alkyl (such as methylethyl, tert-butyl), ($C_1$–$C_{20}$)-alkenyl (such as allyl), substituted alkyl (such as ($C_1$–$C_4$)-alkoxyalkyl, ($C_1$–$C_4$)-alkylthioalkyl, phenetyl, 2,2,2-trichloroethyl, 2-oxo-5-methyl-1,3-dioxolene-4-yl)methyl, benzyl, p-methoxybenzyl, p-nitrobenzyl, o-nitrobenzyl, bis(methoxyphenyl)-methyl, 3,4-dimethoxybenzyl, benzhydryl, trityl, 2-trimethylsilylethyl), substituted silyl (such as trimethylsilyl, tert-butyldimethylsilyl), phthalidyl etc., b) a radical which may be presented in a following form

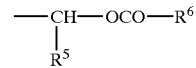

wherein $R^5$ represents hydrogen or a lower alkyl with 1 to 4 carbon atoms, $R^6$ represents hydrogen, alkyl, cycloalkyl, alkoxy, cycloalkoxy, cycloalkylalkyl, alkenyloxy, phenyl, so that the compounds of the formula I are biologically degradable esters, which are known from the group of cefalosporin antibiotics as prodrug agents (such as 1-pivaloyloxymethyl, 1-pivaloyloxyethyl, acetoxyethyl, 1-acetoxyethyl, 1-methoxymethylethylcarbonyloxymethyl, 1-(1-methoxy-1-methylethylcarbonyloxy)ethyl, 1-benzoyloxyethyl, 1-(isopropoxycarbonyloxy)-ethyl, cyclohexyloxycarbonyloxymethyl esters).

The invention relates to novel ethylene derivatives of tricyclic carbapenems of the general formula I in the form of pure diastereoisomers and in the form of pure geometric isomers. The compounds of the formula I comprise at least 2 pure geometric isomers when the methyl group in the ethylidene substituent in 6 position of the carbapenem ring of the compound of the formula I is configured around a double bond as (Z) or as (E) and at least 2 pure diastereoisomers since a new chiral centre in 4 position, which is formed in a joint point with the new ring, may be configured as (R) or as (S). In Scheme 1 and in all further schemes the bold bond represents the position above the level of the sheet and the broken line represents the position under the level of the sheet. The mark (R) or (S) depends on the kind of ring marked C and on the substituents bound to the ring marked C and is determined according to Cahn-Ingold-Prelog rule (Cahn et al., Experientia 12, (1956) 81).

The configuration in 5 position in the joint point of the four- and five-ring of the compound of the general formula I is always the same and is always under the level of the sheet and the mark (R) or (S) is determined according to the above-mentioned Cahn-Ingold-Prelog rule.

Scheme 1: Novel ethylidene derivatives of tricyclic carbapenems in the form of pure geometric isomers and in the form of pure diasteroisomers

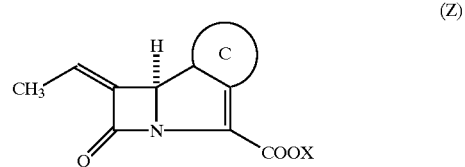

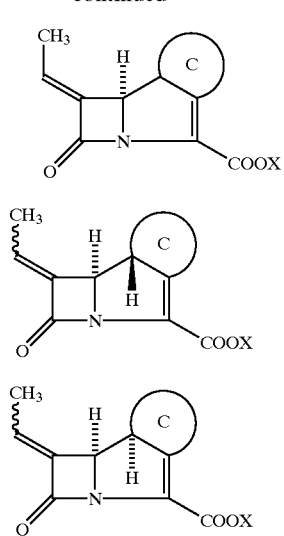

The following compounds of the formula I are especially important as inhibitors of the action of enzymes β-lactamases and/or as antibiotics:

(8S,9R)-10-((E)-ethylidene)-11-oxo-1-azatricyclo[7.2.0.0$^{3,8}$]undec-2-ene-2-carboxylic acid, a pharmaceutically acceptable salt or ester thereof, (8R,9R)-10-((E)-ethylidene)-11-oxo-1-azatricyclo[7.2.0.0$^{3,8}$]undec-2-ene-2-carboxylic acid, a pharmaceutically acceptable salt or ester thereof, (8S,9R)-10-((E)-ethylidene)-11-oxo-1-aza-6-thiatricyclo[7.2.0.0$^{3,8}$]undec-2-ene-2-carboxylic acid, a pharmaceutically acceptable salt or ester thereof, (8R,9R)-10-((E)-ethylidene)-11-oxo-1aza-6-thiatricyclo[7.2.0.0$^{3,8}$]undec-2-ene-2-carboxylic acid, a pharmaceutically acceptable salt or ester thereof.

The compounds of the formula I in the form of an acid and of pharmaceutically acceptable salts or esters thereof are used as antibacterial agents having bacteriostatic and bactericide action upon gram-positive and/or gram-negative bacteria or upon other infects and are used in the prevention and treatment of infectious diseases in humans and animals. The object of the invention is thus also the use of compounds of formula I and of pharmaceutically acceptable salts or esters thereof in the treatment of bacterial diseases in humans and animals, which diseases are caused by gram-positive and/or gram-negative bacteria and other microorganisms.

The compounds of the formula I in the form of an acid and of pharmaceutically acceptable salts or esters thereof are used also and especially as inhibitors of enzymes β-lactamases in a pharmaceutical formulation or in a pharmaceutical formulation in combination with other β-lactam antibiotics such as penicillins and cefalosporins. Thus there may be achieved an effective antibacterial action also upon microorganisms resistant to β-lactam antibiotics. The mechanism of action of enzymes β-lactamases is already well investigated (J. Knowles, Acc. Chem. Res. 18, (1985) 97) and may be described in short as a hydrolysis of the amide bond of β-lactam antibiotic thus losing its ability to inhibit the enzyme D,D-peptidase, this ability being a condition for the antibiotic action of a β-lactam antibiotic. The process of inhibition of the enzyme β-lactamase takes place in two steps. The first step is acylation which generates a tetrahedron complex between a β-lactam inhibitor in Ser70 site in the protein sequence, and this causes a blocade of the active site of the enzyme responsible for the action upon an antibiotic. The second step is deacylation which takes place via action of water and amino acid residues of the active site of the enzyme β-lactamase upon a covalently bound inhibitor-enzyme complex. The whole inhibition process is similar to a process wherein the same enzyme decomposes β-lactam antibiotics (essential differences existing only in the kinetics of the first and the second process steps) and thus the structures of β-lactam antibiotics and inhibitors of the enzyme β-lactamase are similar.

It is characteristic for antibiotics of penam, carbapenem, cefem and carbacefem types that they are substituted with acylamino groups or with a 1-hydroxyethyl group in 6 positions (penams) and 7 positions (cefems), yet these compounds show a relatively poor inhibitory action upon the enzyme -lactamase. Also for such compounds from the field of tricyclic carbapenems (as disclosed in EP-A-0422596) only an antibiotic action has been known so far. It has been shown that the 6 position in the inhibitors of the enzyme β-lactamase must be differently substituted. 6-Ethylidene substituted carbapenems were found to be available systems since they may be obtained from intermediates that are also used in the synthesis of carbapenem antibiotics. Although no compound among them has hitherto been known to act as an inhibitor of the enzyme β-lactamase, it has been found by means of the method of molecular modeling i.e. by calculations and comparison of electronic densities of inhibitors of the enzymes β-lactamases in clinical use and of substrates of β-lactamases of penem and cefem types (D. Kocjan and T. Šolmajer, QSAR and Molecular Modeling, Ed. F. Senz, J. Ginaldo and F. Monant, Computational Tools and Biological Applications, Prous Science Publishers, Barcelona 1995, pp. 335–337) that the calculated distribution of electronic density of the compounds of the formula I and of pharmaceutically acceptable salts or esters thereof could be suitable for inhibitory action upon the enzyme β-lactamase. It has surprisingly been found that the compounds of the formula I according to the invention are active as inhibitors of the enzyme β-lactamase and thereby they differ from the known carbapenem antibiotics disclosed in the literature. The results of testing the inhibitory action of the compounds of the formula I also confirm their inhibitory action upon the enzyme β-lactamase.

Determination of inhibitory action of the compounds of the formula I upon the enzyme β-lactamase The inhibitory action of the compounds of the formula I was determined according to standard methodology (Bush, K. and Sykes, R. B. Methods of Enzymatic Analysis, Third Edition, Vol. 4, p. 280, Verlag Chemie GmbH, Weinheim, 1984). The method comprises a spectrophotometric quantitative (band at 495 nm) measurement of catalytic action of the enzyme β-lactamase from the *E. coli* EC 3.5.2.6 strain. As a substrate nitrocefin ((7R)-3-((E)-2,4-dinitrostiryl)-7-(2-thienylacetamido)-3-cefem-4-carboxylic acid) was used which has the broadest spectrum of susceptibility and sensibility. The hydrolysis of nitrocefin in the presence of an inhibitor of the enzyme β-lactamase was determined.

Hydrolysis of nitrocefin with β-lactamase of *Escherichia coli* 3.5.2.6 in the presence of inhibitors Experimental Data:

| | |
|---|---|
| the concentration of the substrate | 190 μmole/l |
| the concentration of the inhibitor | 10 μmole/l |

-continued

| Inhibitor | Results Inhibitory activity (%) |
|---|---|
| / | 0 |
| compound A | 38 |
| compound B | 23 |
| sulbactam | 50 |

Legend:
/no inhibitor
compound A sodium (8R,9R)-10-((E)-ethylidene)-11-oxo-1-aza-6-thiatricyclo[7.2.0.0$^{3,8}$]undec-2-ene-2-carboxylate
compound B sodium (8S,9R)-10-((E)-ethylidene)-11-oxo-1-azatricyclo[7.2.0.0$^{3,8}$]undec-2-ene-2-carboxylate The object of the invention is thus also the use of the compounds of the formula I, pharmaceutically acceptable salts or esters thereof as inhibitors of the enzyme β-lactamase in human and veterinary medicine.

The invention also relates to pharmaceutical formulations for the treatment of infections in humans and animals, which formulations contain as an active ingredient a therapeutically active amount of a compound of the formula I in the form of an acid or of pharmaceutically acceptable salt or ester thereof, optionally in a combination with a β-lactam antibiotic, together with pharmaceutically acceptable carriers and other pharmaceutically acceptable auxiliary substances for peroral, parenteral, rectal, topical, ophthalmological, nasal or genito-urinary applications in human and veterinary medicine.

Parenteral pharmaceutical formulations according to the invention are stored in ampoules in the form of suspensions, emulsions or solutions in oily carriers or in water together with auxiliary substances such as suspending agents, stabilizers, dispersants and/or preservatives, or in containers with a lid, optionally together with added preservative in the form of a powder, and the contents are dissolved before use in a solvent, most frequently in pyrogen-free water. Parenteral pharmaceutical preparations according to the invention may be applied intravenously or intramuscularly.

Pharmaceutical formulations according to the invention may be used perorally in the form of solid formulations such as tablets, capsules, pastilles, pills, granules, powders together with binders such as syrup, arabic gum, gelatine, sorbitol, tragacanth and polyvinylpyrrolidone, with fillers such as lactose, saccharose, corn starch, calcium phosphate, sorbitol, glycine, with lubricants such as magnesium stearate, talc, polyethylene glycol, silica, with disintegrants such as potato starch, and wetting agents such as sodium lauryl sulfate. Tablets and granules may be also coated with a suitable film according to known processes. Peroral pharmaceutical formulations according to the invention may also be used in liquid forms such as oily suspensions, solutions, emulsions, syrups, together with antioxidants, preservatives, binders, wetting agents, lubricants, thickeners, flavours and aromas. Solid and liquid formulations may be prepared according to generally known methods applicable for preparing pharmaceutical formulations.

Pharmaceutical formulations according to the invention may also be used in the form of suppositories containing usual carriers and other pharmaceutically acceptable auxiliary substances for application in human and veterinary medicine.

Suitable antibiotics which are optionally used in a pharmaceutical formulation according to the invention are not only those antibiotics which are susceptible to degradation by β-lactamases, but also antibiotics having a high degree of resistance to some β-lactamases. As penicillins benzylpenicillin, phenoxymethylpenicillin, ampicillin, amoxycillin, carbencillin etc. may be used and as cefalosporins cefalexin, cefaclor, cefadroxyl, cefpyramid, ceftriaxone, cefixim etc. may be used. When the compounds of the formula I in the form of an acid or of pharmaceutically acceptable salts or esters thereof are combined with another antibiotic in the pharmaceutical formulation, the weight ratio between the compound of the formula I or the pharmaceutically acceptable salt or ester thereof and the antibiotic is in the range from 10:1 to 1:20 and in an amount from 0.1 mg to 1000 mg.

The amount of the compound of the formula I in the form of an acid or of pharmaceutically acceptable salt or ester thereof in pharmaceutical formulations according to the invention is in the range between 0.05 and 100 mg of the active substance per kg of body weight or animal weight, preferably between 0.1 and 40 mg of the active substance per kg of body weight or animal weight. Pharmaceutical formulations according to the invention may be applied from one to four times a day depending upon the way of the application and upon the health condition of the patient.

The invention also relates to novel processes for the preparation of novel compounds of the formula I.

Compounds of the formula I may be prepared in such a way that a compound of the formula II

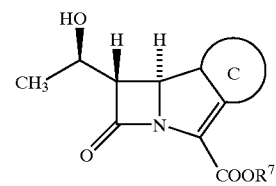

II wherein R$^7$ represents an easily removable ester protective group such as alkyl, benzyl, 4-nitrobenzyl, tert-butyl group and the ring marked C has the meaning given in the compound of the formula I, is converted to a compound of the formula I in three steps according to novel processes hitherto not disclosed in the literature for tricyclic carbapenems.

Step 1

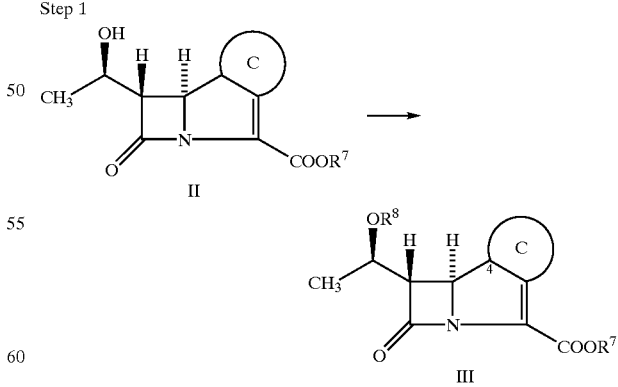

In the first step the hydroxy group of the compound of the formula II is converted into a more easily leaving group, which is better suitable for elimination, in such a way that a compound of the formula III is formed, wherein the radical R$^8$ may be:

an acyl radical from an aliphatic acid, usually aliphatic acid with 1 to 10 carbon atoms, and preferably $R^8$ means acetyl radical, an alkanesulfonyl radical from an alkanesulfonic acid and usually $R^8$ may mean alkanesulfonyl with 1 to 10 carbon atoms which may be once or several times substituted on carbon atoms, preferably with halo, such as fluoro, and preferably $R^8$ means methanesulfonyl, ethanesulfonyl, fluoromethanesulfonyl, trifluoromethanesulfonyl, an arenesulfonyl radical from arenesulfonic acid and usually $R^8$ may mean benzenesulfonyl which may be once or several times substituted, preferably in para position (as p-toluenesulfonyl), or naphthalenesulfonyl, heteroarenesulfonyl radical from heteroarenesulfonic acid and preferably $R^8$ means quinoline-8-sulfonyl.

The conversion of a compound of the formula II to a compound of the formula III may be best carried out in two ways, which, however, does not exclude other ways known in the literature. The reaction is carried out at a temperature from −78° C. to the reflux temperature of the solvent, preferably between −20° C. and room temperature, and reactants are most frequently added to the reaction mixture at a temperature from −20° C. to 0° C., and later on the temperature may rise to room temperature. The reaction may be completed immediately after adding the last reactant, in 24 hours at the latest, usually after 10 to 120 minutes.

According to the first method the reaction of a compound of the formula II to a compound of the formula III is carried out by means of a reactive acid derivative in the presence of a base in an inert organic solvent. As the reactive acid derivative reactive derivatives of carboxylic or sulfonic acids may be used such as acid halides $R^8X'$, wherein X' represents halo, preferably chloro, and preferable reactants are methanesulfonyl chloride, p-toluenesulfonyl chloride, acid anhydrides $(R^8)_2O$, preferably acetanhydride, trifluoromethane sulfonanhydride. As bases there may be used organic nitrogen bases such as mono, di or trisubstituted alkylamines, preferably triethylamine, diethyl isopropylamine, N,N,N',N'-tetramethylethylene diamine, or amidines such as 1,8-diazabicyclo[5.4.0]undec-7-ene, 1,5-diazabicyclo[4.3.0]non-5-ene, or aromatic bases such as pyridine, imidazole, 4-dimethylaminopyridine. As inert organic solvents there may be used inert solvents such as ethers, preferably tetrahydrofuran, dioxan, aromatic hydrocarbons such as benzene, toluene, heterocycles such as pyridine, acetonitrile, and preferably as inert organic solvents chlorinated solvents are used, preferably dichloromethane. As the inert organic solvent also a compound may be used which simultaneously participates in the reaction also in the function of a reactive acid derivative such as compounds N,N-dimethylformamide and N,N-dimethylacetamide.

According to the second method the reaction of a compound of the formula II to a compound of the formula III is carried out by means of the acid $R^8OH$ which is bound with condensation agents (reactants for elimination of water) to hydroxy group in 4 position of a compound of the formula III, preferably in the same organic solvents as disclosed in the first method. As condensation agents N,N'-carbonylimidazole, diphenylphosphorylazide, diphenylphosphorylcyanide, carbodiimides such as dicyclohexylcarbodiimide, N-ethyl-N'-(3-dimethylaminopropyl)-carbodiimide, diazacarboxylates in the presence of phosphines (reaction according to Mitsunobu, O. Mitsunobu, Synthesis 1981, 1), preferably diethyl diazadicarboxylate in the presence of triphenylphosphine, may be used. Besides this method also other methods suitable for elimination of water may be used.

Step 2

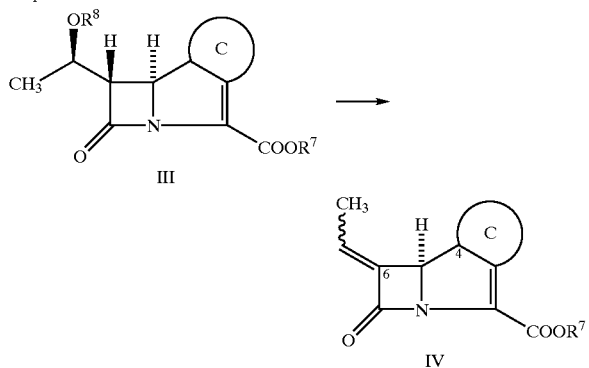

In the second step of the conversion of a compound of the formula II to a compound of the formula I, a substituent $R^8$ from a compound of the formula III is cleaved by means of base-catalyzed elimination to obtain a compound of the formula IV. In the reaction as the base there may be used inorganic bases (such as alkali metal carbonates), organic bases such as alkali metal salts of alcohols (such as sodium methoxide, sodium ethoxide, potassium tert-butoxide) and of amides (such as lithium bis(trimethysilyl)amide, lithium diisopropylamide), alkyl metals (such as butyllithium), aryl metals (such as phenyllithium), organic amines (such as triethyl amine, ethyl diisopropylamine, tetramethylethylenediamine), amidines (such as 1,8-diazabicyclo[5.4.0]undec-7-ene, 1,5-diazabicyclo[4.3.0]non-5-ene), preferably bases of amidine type are used in the reaction as strong non-nucleophilic bases which are soluble in aprotic organic solvents. As a solvent an inert organic solvent is used such as alcohols (such as methanol, ethanol, tert-butanol, yet not in the case when amides, alkyl metals and aryl metals are used as bases), hydrocarbons such as aromatic hydrocarbons (such as benzene, toluene), ketones (such as acetone), esters (such as ethyl acetate), acetonitrile, amides (such as N,N-dimethylformamide, N,N-dimethylacetamide, hexamethylphosphoric triamide), dimethyl sulfoxide, preferably ethers such as tetrahydrofuran, dioxan, and chlorinated solvents such as dichloromethane, chloroform, dichloroethane. The reaction is carried out at temperatures from −78° C. to the reflux temperature of the solvent, preferably at a temperature between −20° C. and room temperature. The reaction may be carried out for 5 minutes to 48 hours, mostly for 1 to 6 hours.

The reaction from a compound of the formula II to a compound of the formula IV may be carried out directly without isolating a compound of the formula III. In these cases the group $R^8O$ is spontaneously cleaved from the compound of the formula III in the following ways:

during the conversion of the compound of the formula II to the compound of the formula III under the influence of a base used in the reaction with a reactive acid derivative, thermically during the conversion of the compound of the formula II to the compound of the formula III with a reactive acid derivative or during the process of isolation of the compound of the formula III (elimination takes place here without the presence of a base), under the influence of the chromatographic carrier (such as silica gel) during the chromatographic purification of the compound of the formula III.

The group R⁸O from a compound of the formula III is cleaved in such a way that the methyl group in the ethylidene substituent in 6 position of carbapenem ring of a compound of the formula IV is configured around the double bond as (Z) or (E) and in most cases the (E) isomer is prevalent.

In the process for preparing a compound of the formula IV also two diasteroisomers 4-(R) and 4-(S) are formed since in 4 position of the carbapenem ring of the compound of the formula IV representing a joint point with the ring marked C, a new chiral centre is formed. Individual diastereoisomers may be separated by chromatographic purification on a chromatographic carrier.

Both diastereoisomers may be separated already at the compound of the formula II in such a way that the synthesis process from the compound of the formula II over the compound of the formula III to the compound of the formula IV is carried out with already separated isomers. When due to certain reasons (such as poor resolution) diastereisomers of the compound of the formula II cannot be separated, individual diasteroisomers may be obtained from diasteroisomeric mixtures of the compounds of the formula III or IV also in later steps in the same way as disclosed above.

Both geometric isomers are isolated by means of chromatographic purification of the isomeric mixture of the compound of the formula IV on silica gel.

The synthesis routes disclosed for preparing compounds of the formula IV do not exclude the use of other methods known from the literature.

Step 3

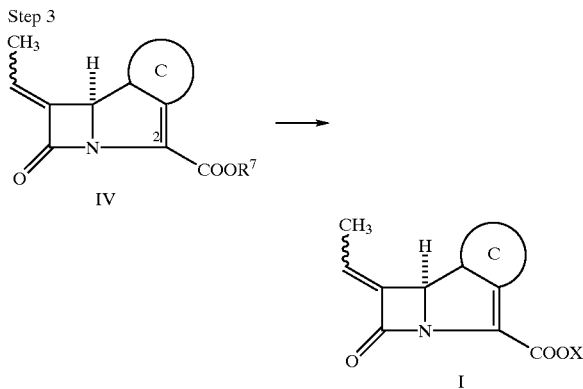

In the last step of the conversion of a compound of the formula II to a compound of the formula I, from a compound of the formula IV an ester protective group R⁷ is eliminated from the substituent COOR⁷ in 2 position of carbapenem ring of the compound of the formula IV according to generally known methods for eliminating a particular protective group. Thus the allyl group is preferably removed with Pd(0) catalysts (preferably tetrakis (triphenylphosphine)palladium (0)) in the presence of phosphine (preferably triphenylphosphine) and under the addition of an alkali metal cation (preferably alkali metal salt of 2-ethylhexanoic acid). Benzyl and 4-nitrobenzyl groups are removed by catalytic hydrogenation in the presence of the alkali metal cation donor (T. W. Green in Protective Groups in Organic Synthesis, John Willey & Sons, New York 1981, p. 191) and as the catalyst preferably palladium on a carrier (such as 10% palladium on active carbon) is used and as the alkali metal cation donor preferably sodium or potassium hydrogen carbonate is used, the product of both kinds of conversions being a compound of the formula I wherein X represents an alkali metal. If the protective group is removed without the presence of a cation, a compound of the formula I in the form of an acid (X represents hydrogen in this case) is isolated and a salt thereof is prepared by neutralization or reprecipitation according to methods known from the literature. The protective group R⁷ may also be removed in the presence of a nitrogen base such as ammonia, amines (such as trimethylamine, triethylamine, N,N'-dibenzylethylenediamine, ethanolamine, diethanolamine, triethanolamine, dicyclohexylamine, 2-piperidinyl), amidines (such as 1,8-diazabicyclo[5.4.0]undec-7-ene, 1,5-diazabicyclo[4.3.0]non-5-ene, 3,3,6,9,9-pentadimethyl-2,10-diazabicyclo[4.4.0]dec-1-ene), guanidines (such as guanidine, cyanoguanidine) or other nitrogen bases (such as 4-dimethylaminopyridine, imidazole) so that in the obtained compound of the formula I X represents the above mentioned protonated nitrogen bases.

When in the ring marked C of the compound of the formula IV there are substituents protected with well-known protective groups, these substituents should, before step 3, be first removed by well-known deprotection methods except in cases when these protective groups are removed with the reactants mentioned in the description of step 3.

The compounds of the formula I in the form of an acid or a salt (X represents an alkali metal) may be converted by methods well-known in the Prior Art to biologically acceptable esters of the formula I (in this case X represents an organic allyl radical, most frequently of the type CHR⁵OCOR⁶).

The disclosed synthesis routes for the conversion of the compound of the formula IV to the compound of the formula I do not exclude the use of other methods described in the literature.

The starting compound of the formula II is prepared from (3R,4R)-4-acetoxy-3-((R)-1-(tert-butyldimethylsilyloxy) ethyl)azetidine-2-one which is commercially available as Azetidon®—Kaneka (Japan) according to known processes disclosed in the literature:

T. Murayama et al., Tetrahedron Lett. 35, (1994) 2271; J. Tsuji, Tetrahedron 42 (1986) 4401; P. J. Reider et al., Tetrahedron Lett. 23, (1982) 379; A. Yoshida et al., Tetrahedron Lett. 25, (1984) 2793; I. Ernest et al., J. Am. Chem. Soc. A0, (1979) 6310; A. Afonso et al., J. Am. Chem. Soc. 104, (1982) 6139; R. Di Fabio et al., Bioorg. Med. Chem. Lett. 5, (1995) 1235; F. A. Corey and R. J. Sundberg, Advanced Organic Chemistry Second Edition, Plenum Press New York and London, 1983, Annual Reports in Organic Synthesis 1975–1989, Academic Press Inc., San Diego; T. W. Green, Protective Groups in Organic Synthesis, John Willey & Sons, New York 1981, p. 45.

The invention is disclosed in detail by the following Examples which in no way should be construed as limitative thereto. Silica gel of the company Merck, trade mark Kieselgel 60, particle size 0.063–0.200, in a 50 to 100 fold amount of the input substance was used for column chromatography and the course of the reactions and preparative chromatography was followed by thin layer chromatography on glas plates of the company Merck, trade mark Kieselgel 60 GF$_{254}$.

EXAMPLE 1

Diallyl 3,3'-thiodipropionate

To a solution of triethylamine (159.6 ml; 0.15 mole) in allyl alcohol (945 ml) 3,3'-thiodipropionyl chloride (44.2 g; 0.2 mole) was slowly added drop by drop. The obtained mixture was stirred for another hour at room temperature and then allyl alcohol was evaporated on rotavapor. To the obtained oily residue after evaporation diethyl ether (800 ml) and 1M hydrochloric acid (400 ml) were added, the solution was stirred and organic and aqueous phases were separated. The aqueous phase was extracted with diethyl ether (2×400 ml), the combined ether phases were washed with water (2×200 ml) and dried with magnesium sulfate. The drying agent was filtered off and the solvent was evaporated from the filtrate on rotavapor. The crude product was distilled at the pressure of 0.8 mbar to obtain the title compound (43.5 g; 82%) in the form of a colourless oil, the temperature interval of distillation being 134–135° C.

IR (film): $v_{max}$ (cm$^{-1}$): 2934, 1738, 1373, 1343, 1243, 1172, 1154, 990. MS (M$^+$): 258.

$^1$H-NMR (300 MHz, TMS, CDCl$_3$): δ: 2.65 (4H, t, J=7.3 Hz), 2.82 (4H, t, J=7.3 Hz), 4.60 (4H, dt, J=4.3 Hz, 1.4 Hz), 5.24 (2H, dq, J=9.1 Hz, 1.3 Hz), 5.32 (2H, dq, J=17.2 Hz, 1.5 Hz), 5.8–6.0 (2H, m).

EXAMPLE 2a

Allyl 4-chlorobutyrate

To a mixture of 4-chlorobutyric acid (48 ml; 0.48 mole), allyl alcohol (200 ml) and hexane (1.2 l) p-toluenesulfonic acid (16.0 g; 0.08 mole) was added. The obtained mixture was heated for 5 hours at reflux temperature in such a way that water was simultaneously removed with Dean-Stark apparatus (Vogel's Textbook of Practical Organic Chemistry, Fourth Ed., Longman, London, 1978, p. 411). The mixture was then cooled to room temperature and shaken with 7% aqueous sodium hydrogencarbonate solution (2×500 ml). The obtained solution was dried with magnesium sulfate and after the filtration of the drying agent hexane was evaporated. The crude residue was distilled under reduced pressure 10 mbar at the temperature of 95° C. and the title compound (61.2 g; 79%) was obtained in the form of a colourless oil.

IR (film): $v_{max}$ (cm$^{-1}$): 2964, 1738, 1733, 1198, 1176, 1146, 909. MS (M$^+$): 162.

$^1$H-NMR (300 MHz, TMS, CDCl$_3$): δ: 2.10 (2H, m), 2.54 (2H, t, J=8 Hz), 3.61 (2H, t, J=8 Hz), 4.58 (2H, dt, J=4 Hz, 1.4 Hz), 5.26 (1H, dq, J=10 Hz, 1.4 Hz), 5.33 (1H, dq, J=17 Hz, 1.4 Hz), 5.91 (1H, m).

EXAMPLE 2b

Allyl 3-chloropropionate

It was proceeded in the same way as in Example 2a. 3-chloropropionic acid (108.5 g; 1.0 mole) was taken and the other reactants were used in the same molar ratios as in Example 2a. The title compound (121.8 g; 82%) was obtained in the form of a colourless liquid with the distillation point 88–91° C. at the pressure of 15 mbar.

IR (film): $v_{max}$ (cm$^{-1}$): 2976, 1750, 1653, 1419, 1387, 1209, 935. MS (M$^+$): 148.

$^1$H-NMR (300 MHz, TMS, CDCl$_3$): δ: 2.82 (2H, t, J=6.65 Hz), 3.77 (2H, t, J=6.65 Hz), 4.63 (2H, m), 5.30 (2H, m), 5.93 (1H, m).

EXAMPLE 3

Allyl 4-(ethoxycarbonylmethylthio)butyrate

Sodium (9.06 g; 0.39 mole) was decomposed in allyl alcohol (380 ml). The obtained solution was treated by dropwise adding of first ethyl mercaptoacetate (42.7 ml; 0.39 mole) at the temperature of 0° C. and then of allyl 4-chlorobutyrate (58.3 g; 0.36 mole) prepared according to the process disclosed in Example 2a. The obtained mixture was stirred for three hours at room temperature and then for 1 hour at reflux temperature. The mixture was concentrated by evaporation and poured into a mixture of diethylether (200 ml) and of an ice/water mixture (100 g). The obtained solution was acidified with 1M hydrochloric acid solution to achieve a pH value of the medium between 3 and 6. The ether phase was separated and the obtained aqueous phase was extracted with diethyl ether (200 ml). The combined ether fractions were washed with water (200 ml) and 4% aqueous sodium hydrogencarbonate solution (200 ml) and dried with magnesium sulfate. After the removal of the drying agent and evaporation of ether, the title compound (78.1 g; 84%) was obtained, which was used in the crude form in the next reaction.

IR (film): $v_{max}$ (cm$^{-1}$): 2941, 1735, 1276, 1170, 1143, 991. MS (M$^+$): 258.

$^1$H-NMR (300 MHz, TMS, CDCl$_3$): δ: 1.29 (3H, t, J=7.2 Hz), 1.95 (2H, m), 2.47 (2H, t, J=7.2 Hz), 2.69 (2H, t, J=7.2 Hz), 3.21 (2H, s), 4.18 (2H, q, J=7.2 Hz), 4.58 (1H, dq, J=5.6 Hz, 1.4 Hz), 5.26 (1H, dq, J=10.4 Hz, 1.3 Hz), 5.32 (1H, dq, J=17.2 Hz, 1.5 Hz), 5.90 (1H, m).

EXAMPLE 4

Mixture of ethyl (2-(allyloxycarbonyl)ethyl) thioacetate and allyl (2-(allyloxycarbonyl)ethyl) thioacetate Sodium (19.7 g; 0.86 mole) was decomposed in allyl alcohol (850 ml). The obtained solution was treated by dropwise adding of first ethyl mercaptoacetate (106.2 ml; 0.86 mole) at the temperature of 0° C. and then of allyl 3-chloropropionate (119.3 g; 0.81 mole) prepared according to the process disclosed in Example 2b. The obtained mixture was stirred for 2 hours at room temperature and then for 2 hours at reflux temperature. After the completed reaction allyl alcohol was evaporated and to the obtained residue after evaporation diethyl ether (400 ml) and water (200 ml) were added. The obtained phases were separated and the resulting aqueous phase was again extracted with diethyl ether (200 ml). The combined ether phases were washed with 5% aqueous sodium carbonate solution and the ether phase and the aqueous phase were again separated. Diethyl ether was evaporated and the residue was redistilled in vacuo at the pressure of 4 mbar. The product (158.5 g; 84%) was obtained as a mixture of the ethyl ester and of the allyl ester of the title compound in a molar ratio of 7:3 in the form of a colourless oil as a fraction with the temperature distillation interval of 155–158° C. The mixture did not need to be separated for further reaction.

IR (film): $v_{max}$ (cm$^{-1}$): 2950, 1726, 1410, 1362, 1271, 1145, 1027, 932. MS (M$^+$): 232, 244.

$^1$H-NMR (300 MHz, TMS, CDCl$_3$): ethyl ester δ: 1.29 (3H, t, J=7.1, Hz), 2.68 (2H, t, J=7.3 Hz), 2.94 (2H, t, J=7.30 Hz), 3.25 (2H, s), 4.21 (2H, q, J=7.1 Hz), 4.61 (2H, m), 5.28 (2H, m), 5.92 (1H, m); allyl ester: δ: 2.68 (2H, t, J=7.3 Hz), 2.94 (2H, t, J=7.3 Hz), 3.28 (2H, s), 4.61 (2H, m), 5.28 (2H, m), 5.92 (1H, m); ratio 7:3.

EXAMPLE 5a

Allyl 4-hydroxy-5,6-dihydro-2H-thiopyrane-3-carboxylate

To a mixture of sodium sand (23 g; 1.0 mole) (Vogel's Textbook of Practical Organic Chemistry, Fourth Ed., Longman, London, 1978, p. 313) and anhydrous diethyl ether (3.4 l), allyl alcohol (65.8 ml) was slowly added. The obtained reaction mixture was stirred for two days at room temperature and then diallyl 3,3'-thiodipropionate (129.0 g; 0.5 mole) prepared according to the process disclosed in Example 1 was slowly added drop by drop. The mixture was stirred for another day at room temperature and then under ice cooling first absolute ethanol (10 ml) and then water (400 ml) and concentrated hydrochloric acid (455 ml) were added and it was stirred until the whole was dissolved. The phases were separated. The obtained organic phase was washed with water (400 ml), a 7% sodium hydrogencarbonate solution (3×400 ml) and once more with water (200 ml). The organic phase was dried with magnesium sulfate, the drying agent was filtered off, the filtrate was evaporated and dried. The title compound (42.4 g; 42%) was obtained as a crude product in the form of a yellowish oil.

IR (film): $\nu_{max}$ (cm$^{-1}$): 2932, 1738, 1646, 1306, 1251, 1224, 1197, 1060. MS (M$^+$): 200.

$^1$H-NMR (300 MHz, TMS, CDCl$_3$): δ: 2.6 (2H, m), 2.78 (2H, t, J=7 Hz), 4.34 (2H, s) 4.68 (1H, dt, J=4 Hz, 1.0 Hz), 5.28 (2H, dq, J=9 Hz, 1.3 Hz), 5.33 (2H, dq, 17 Hz, 1.5 Hz), 5.85 (1H, s), 6.05 (1H, m).

EXAMPLE 5b

Allyl 3-hydroxy-5,6-dihydro-4H-thiopyrane-2-carboxylate

The procedure was carried out in the same way as in Example 5a. Allyl 4-(ethoxycarbonylmethylthio)butyrate (73.8 g; 0.29 mole) prepared according to the process disclosed in Example 3 was taken and the other reactants were used in the same molar ratios as in Example 5a. The title compound (26.1 g; 46%) in the form of a yellowish oil was obtained. The title compound in the crude form was used in the further reaction.

IR (film): $\nu_{max}$ (cm$^{-1}$): 2956, 2930, 2857, 1769, 1713, 1258, 1141, 836. MS (M$^+$): 200.

$^1$H-NMR (300 MHz, TMS, CDCl$_3$): δ: 2.12 (2H, m), 2.41 (2H, t, J=6.6 Hz), 2.69 (2H, t, J=5.5 Hz), 4.71 (1H, dd, 5.1 Hz, <1 Hz), 5.28 (1H, dt, 10.2 Hz, <1 Hz), 5.38(1H, dt, 16.2 Hz, 1.4 Hz), 5.85–6.05 (1H, m), 12.15 (1H, s).

EXAMPLE 5c

Allyl 3-hydroxy-4,5-dihydrothiophene-2-carboxylate

The procedure was carried out in the same way as in Example 5a. A mixture (79.0 g) of ethyl ester and allyl ester of (2-(allyloxycarbonyl)ethyl)thioacetate prepared according to the process disclosed in Example 4 was taken and the other reactants were used in the same molar ratios as in Example 5a. The title compound (47.5 g; 46%) in the form of a yellowish oil was obtained. The compound did not need to be purified for the further process.

IR (film): $\nu_{max}$ (cm$^{-1}$): 2920, 1718, 1656, 1320, 1271, 1222, 1143, 778. MS (M$^+$): 186.

$^1$H-NMR (300 MHz, TMS, CDCl$_3$): δ: 3.35 (2H, m), 3.80 (2H, m), 4.68 (2H, m), 5.30 (2H, m), 5.92 (1H, m), 10.95 (1H, s).

EXAMPLE 6a (3S,4S)-3-((R)-(1-(tert-butyldimethylsilyl)oxy)ethyl)-4-((3RS)-allyloxycarbonyl-4-oxotetrahydro-4H-thiopyrane-3-yl)azetidine-2-one To a mixture of 60% sodium hydride (3.84 g; 0.096 mole) and anhydrous tetrahydrofuran (125 ml), a solution of allyl 4-hydroxy-5,6-dihydro-2H-thiopyrane-3-carboxylate (19.22 g; 0.096 mole) prepared according to the process disclosed in Example 5a in anhydrous tetrahydrofuran (80 ml) was added drop by drop under ice cooling for 10 minutes. The obtained mixture was stirred for 1 hour at room temperature and then under vigorous shaking (3R,4R)-4-acetoxy-3-((R)-(1-tert-butyl-dimethylsilyl)oxy)ethyl)azetidine-2-one (27.8g; 0.096 mole) (Azetidon®—Kaneka (Japan)) was added in one portion. The obtained mixture was stirred for another hour at room temperature. To the mixture diethyl ether (400 ml) and water (400 ml) were added and the obtained mixture was acidified with a concentrated hydrochloric acid to a pH value of the medium from 3 to 6. The obtained phases were separated and the obtained aqueous phase was extracted with diethyl ether (2×200 ml). The combined ether phases were then washed with a 7% aqueous sodium hydrogencarbonate solution (200 ml) and dried with magnesium sulfate. The drying agent was filtered off and the filtrate was evaporated. The crude product was purified by column chromatography (silica gel, diethyl ether/petroleum ether 1:1 (v/v)) to obtain a diastereoisomeric mixture (15.91 g; 39%) of the title compound. The isomers might be separated and isolated by column chromatography, but it was not necessary for the further process. For the further process the mixture of both diastereoisomers was used.

First fraction at chromatographic separation:

The diastereoisomer was in the form of a viscous oil.

IR (film): $\nu_{max}$ (cm$^{-1}$): 2956, 2930, 2857, 1769, 1713, 1258, 1141, 836. MS (M$^+$): 427.

$^1$H-NMR (300 MHz, TMS, CDCl$_3$): δ: 0.06 (3H, s), 0.08 (3H, s), 0.88 (9H, s), 1.21 (6H, d, J=7 Hz), 2.72 (1H, d, J=14 Hz), 2.8–3.0 (4H, m), 3.26 (2H, dd, J=14 Hz, 3 Hz), 3.29 (1H, dd, J=5.2 Hz, 2.2 Hz), 3.95 (1H, dt, J=2.2 Hz, <1 Hz), 4.10–4.25 (1H, m), 4.71 (2H, dt, J=6.0 Hz, 1.2 Hz), 5.29 (1H, ddd, J=10.3 Hz, 2.2 Hz, 1.0 Hz), 5.35 (1H, dd, J=17.2 Hz, 2.8 Hz, 1.4 Hz), 5.8–5.95 (1H, m), 6.01 (1H, s).

Second fraction at chromatographic separation:

The diastereoisomer was in the form of white crystals with m.p. 117–119° C. (cyclohexane).

IR (KBr): $\nu_{max}$ (cm$^{-1}$): 3378, 2956, 2931, 2857, 1771, 1710, 1375, 1279, 1096. MS (M$^+$): 427.

$^1$H-NMR (300 MHz, TMS, CDCl$_3$): δ: 0.06 (3H, s), 0.08 (3H, s), 0.84 (9H, s), 0.96 (6H, d, J=7 Hz), 2.7–2.9 (4H, m), 3.11 (1H, d, J=15 Hz), 3.13 (1H, t, J=2.5 Hz), 3.22 (2H, dd, J=15 Hz, 3 Hz), 4.17–4.21 (1H, m), 4.31 (2H, d, J=2.5 Hz), 4.6–4.72 (1H, m), 5.25 (2H, ddd, J=10.5 Hz, 1 Hz, <0.8 Hz), 5.32 (2H, ddd, J=19 Hz, 1 Hz, <0.8 Hz), 5.8–5.95 (1H, m), 5.93 (1H, s).

EXAMPLE 6b (3S,4S)-3-((R)-(1-(tert-butyldimethylsilyl)oxy)ethyl)-4-((2RS)-allyloxycarbonyl-3-oxo-tetrahydrothiopyrane-2-yl)azetidine-2-one The procedure was carried out in the same way as in Example 6a until the isolation of the title compound in a crude form. Allyl 3-hydroxy-5,6-dihydro-4H-thiopyrane-2-carboxylate (24.4 g; 1.22 mole) prepared according to the process disclosed in Example 5b was taken and the other reactants were used in the same molar ratios as in Example 6a. The crude product was then purified by column chromatography (silica gel, diethyl ether/petroleum ether 2:1 (v/v) with gradient to diethyl ether) to obtain a diastereoisomeric mixture (32.1 g; 62%) of the title compound. The mixture of both diastereoisomers was used for the further process.

First fraction at chromatographic separation:

The diastereoisomer was in the form of white crystals with m.p. 87–91° C. (cyclohexane).

IR (KBr): $v_{max}$ (cm$^{-1}$): 2954, 2933, 2859, 1760, 1703, 1232, 836. MS (M$^+$): 427.

$^1$H-NMR (300 MHz, TMS, CDCl$_3$): δ: 0.02 (6H, s, s), 0.83 (9H, s), 1.19 (3H, d, J=7.3 Hz), 2.2–2.5 (2H, m), 2.54–2.64 (3H, m), 2.87 (1H, ddd, J=14.4 Hz, 12.2 Hz, 3.0 Hz), 3.20 (1H, t, J=1.9 Hz), 4.07 (1H, d, J=1.9 Hz), 4.1–4.2 (1H, m), 4.68 (2H, d, J=5.7 Hz), 5.15 (1H, m, J=10.2 Hz), 5.31 (1H, dd, J=17.1 Hz, 1.2 Hz), 5.8–6.0 (2H, m).

Second fraction at chromatographic separation:

The diastereoisomer was in the form of white crystals with m.p. 109–113° C. (hexane).

IR (KBr): $v_{max}$ (cm$^{-1}$): 3415, 3402, 2956, 2931, 2858, 1767, 1709, 1220, 1193, 838, 777. MS (M$^+$): 427.

$^1$H-NMR (300 MHz, TMS, CDCl$_3$): δ: 0.1 (6H, s), 0.83 (9H, s), 0.95 (3H, d, J=7.3 Hz), 2.2–2.7 (5H, m), 2.94 (1H, ddd, J=14.7 Hz, 11.8 Hz, 2.9 Hz), 3.19 (1H, m, 2.2 Hz), 3.26 (1H, m), 4.1–4.2 (1H, m), 4.36 (1H, d, J=1.7 Hz), 4.6–4.7 (2H, m), 5.28 (2H, dd, J=10.3 Hz, 0.8 Hz), 5,35 (1H, ddd, J=17.1 Hz, 1.2 Hz, 0.5 Hz), 5.80 (1H, s), 5.85–6.1 (2H, m).

EXAMPLE 6c (3S,4S)-3-((R)-(1-(tert-butyldimethylsilyl)oxy) ethyl)-4-((2RS)-anyloxycarbonyl-3-oxo-tetrahydrothiene-2-yl)azetidine-2-one The procedure was carried out in the same way as in Example 6a up to the isolation of the title compound in crude form. Allyl 3-hydroxy-4,5-dihydrothiophene-2-carboxylate (40.0 g; 0.21 mole) prepared according to the process disclosed in Example 5c was taken and the other reactants were used in the same molar ratios as in Example 6a. The crude product was then purified by column chromatography (silica gel, diethyl ether/petroleum ether 1:1 (v/v)) to obtain a diasteroisomeric mixture (36.1 g; 41%) of the title compound. The mixture of both diastereoisomers was used for the further process.

First fraction at chromatographic separation:

The diastereoisomer was in the form of white crystals with m.p. 114–116° C. (hexane).

IR (KBr): $v_{max}$ (cm$^{-1}$): 3174, 2935, 1760, 1726, 1218, 1138, 828, 776. MS (M$^+$): 413.

$^1$H-NMR: (300 MHz, TMS, CDCl$_3$): δ: 0.04 (6H, s), 0.84 (9H, s), 1.09 (3H, d, J=6.48 Hz), 2.68 (1H, m), 2.95 (2H, m), 3.20 (1H, m), 3.28 (1H, m), 4.20 (1H, dd, J=6.40 Hz), 4.24 (1H, d, J=1.95 Hz), 4.65 (2H, m), 5.28 (2H, dt), 5.85 (1H, m), 6.11 (1H, s).

Second fraction at chromatographic separation:

The diastereoisomer was in the form of white crystals with m.p. 79–80° C. (hexane).

IR (KBr): $v_{max}$ (cm$^{-1}$): 3165, 2920, 1757, 1735, 1220, 832. MS (M$^+$): 413.

$^1$H-NMR: (300 MHz, TMS, CDCl$_3$): δ: 0.03 (3H, s), 0.04 (3H, s), 0.84 (9H, s), 1.22 (3H, d, J=6.3 Hz), 2.71 (1H, m), 2.93 (1H, m, J=5.6 Hz), 2.95 (2H, m), 3.15 (1H, m), 4.25 (1H, m), 4.63 (1H, d, J=5.6 Hz), 4.65 (2H, m), 5.28 (2H, dt), 5.85 (1H, m), 5.83 (1H, s).

EXAMPLE 7a (3S,4S)-3-((R)-(1-(tert-butyldimethylsilyl)oxy) ethyl)-4-((3RS)-4-oxotetrahydro-4H-thiopyrane-3-yl)azetidine-2-one (3S,4S)-3-((R)-(1-(tert-butyldimethylsilyl)oxy)ethyl)-4-((3RS)-allyloxycarbonyl-4-oxo-tetrahydro-4H-thiopyrane-3-yl)azetidine-2-one (15.9 g; 0.037 mole) prepared according to the process disclosed in Example 6a was dissolved in a 0.67 M triethylammonium formate solution (112 ml) in dichlorometane. To the obtained solution triphenylphosphine (1.01 g; 3.9 mmole) and tetrakis(triphenylphosphine)-palladium(0) (1.16 g; 1.0 mmole) prepared according to the process disclosed in D.R. Coulson, Inorganic Synthesis 13, 121 (1972) were added. After stirring for 1 hour at room temperature, dichloromethane (170 ml) was added and the mixture was shaken with 1M hydrochloric acid solution (80 ml). The obtained phases were separated and the obtained aqueous phase was extracted with dichloromethane (80 ml). The combined organic phases were washed with water (80 ml), then with 7% aqueous sodium hydrogencarbonate solution (80 ml), afterwards dried with magnesium sulfate and after filtering off the drying agent the filtrate was evaporated. The crude product was purified with column chromatography (silica gel, ether/petroleum ether 3:1 (v/v)). Separated diastereoisomers with the common yield of 75% were obtained.

(3S,4S)-3-((R)-(1-(tert-butyldimethylsilyl)oxy)ethyl)-4-((3R)-4-oxotetrahydro-4H-thiopyrane-3-yl)azetidine-2-one The title compound (1.21 g; 9%) in the form of white crystals with m.p. 148–151° C. (hexane) was formed.

IR (KBr): $v_{max}$ (cm$^{-1}$): 3240, 2957, 2928, 2857, 1757, 1718, 1105, 963. MS (M$^+$): 343.

$^1$H-NMR (300 MHz, TMS, CDCl$_3$): δ: 0.04 (6H, d, J=3.7 Hz), 0.84 (9H, s), 1.18 (3H, d, J=6.3 Hz), 2.68–2.76 (2H, m), 2.84–3.0 (6H, m), 4.14–4.24 (2H, m), 5.86 (1H, s).

(3S,4S)-3-((R)-(1-(tert-butyldimethylsilyl)oxy)ethyl)-4-((3S)-4-oxotetrahydro-4H-thiopyrane-3-yl)azetidine-2-one The title compound (8.48 g; 66%) in the form of white crystals with m.p. 142–144° C. (hexane) was formed.

IR (KBr): $v_{max}$ (cm$^{-1}$): 2950, 2928, 2855, 1758, 1733, 1703, 1371, 1060, 964. MS (M$^+$): 343.

$^1$H-NMR (300 MHz, TMS, CDCl$_3$): δ: 0.04 (6H, s), 0.85 (9H, s), 1.23 (3H, d, J=6.2 Hz), 2.6–2.8 (5H, m), 2.9–3.0 (3H, m), 3.62 (1H, dd, J=2.15 Hz, 9.5 Hz), 4.14 (1H, m), 6.05 (1H, s).

EXAMPLE 7b (3S,4S)-3-((R)-(1-(tert-butyldimethylsilyl)oxy) ethyl)-4-((3RS)-3-oxotetrahydrothiopy-rane-2-yl) azetidine-2-one The procedure was carried out in the same way as in Example 7a up to the isolation of the title compound in crude form. A diastereoisomeric mixture (5.16 g; 0.012 mole) of (3S,4S)-3-((R)-(1-(tert-butyldimethylsilyl)oxy)ethyl)-4-((2RS)-allyloxy carbonyl-3-oxotetrahydrothiopyrane-2-yl) azetidine-2-one prepared according to the process disclosed in Example 6b was taken and the other reactants were used in the same molar ratios as in Example 7a. The crude product was then purified by column chromatography (silica gel, diethyl ether) to obtain separated diastereoisomers with the common yield of 48%.

(3S,4S)-3-((R)-(1-(tert-butyldimethylsilyl)oxy)ethyl)-4-((3R)-3-oxotetrahydrothiopyrane-2-yl)azetidine-2-one The title compound (0.61 g; 15%) was obtained in the form of a yellow oil.

IR (film): $v$,. (cm$^{-1}$): 2959, 2933, 2859, 1760, 1710. MS (M$^+$): 343.

$^1$H-NMR (300 MHz, TMS, CDCl$_3$): δ: 0.02 (6H, s), 0.82 (9H, s), 1.16 (3H, d, J=6.3 Hz), 2.3–2.45 (2H, m), 2.47–2.56 (2H, m), 2.72–2.83 (1H, m), 2.76–2.96 (1H, m), 3.07 (1H, dd, J=5.3 Hz, 2.2 Hz), 3.62 (1H, d, J=4.7 Hz), 4.11 (1H, dd, J=4.7 Hz, 2.2 Hz), 4.16 (1H, m), 6.05 (1H, s).

(3S,4S)-3-((R)-(1-(tert-butyldimethylsilyl)oxy)ethyl)-4-((3S)-3-oxotetrahydrothiopyrane-2-yl)azetidine-2-one The title compound (1.36 g; 33%) was obtained in the form of a yellow oil.

IR (film): vmax (cm$^{-1}$): 2960, 2858, 1755, 1709. MS (M$^+$): 343.

$^1$H-NMR (300 MHz, TMS, CDCl$_3$): δ: 0.0 (1H, s), 0.81 (9H, s), 1.14 (3H, d, J=6.4 Hz), 2.2–2.4 (2H, m), 2.4–2.6 (2H, m), 2–6–2.72 (1H, m), 2.82–2.86 (1H, m), 2.9–3.0 (1H, m), 3.48 (1H, d, J=10.0 Hz), 3.75 (1H, dd, J=10.0 Hz, 2 Hz), 4.13 (1H, m), 6.3 (1H, m).

EXAMPLE 7c (3S,4S)-3-((R)-(1-(tert-butldimethylsilyl)oxy)ethyl)-4-((2RS)-3-oxotetrahydrothiene-2-yl)azetidine-2-one The procedure was carried out in the same way as in Example 7a up to the isolation of the title compound in the crude form. The diastereoisomeric mixture (30.0 g; 0.073 mole) of (3S,4S)-3-((R)-(1-(tert-butyldimethylsilyl)oxy)ethyl)-4-((2RS)-allyloxycarbonyl-3-oxotetrahydrothienyl-2-yl)azetidine-2-one prepared according to the process disclosed in Example 6c was taken and the other reactants were used in the same molar ratios as in Example 7a. The crude product was then purified by column chromatography (silica gel, diethyl ether/petroleum ether 2:1 (v/v)) to obtain diastereoisomeric mixture (6.34 g; 26%) of the title compound in the form of white crystals with m.p. of the mixture 105–108° C. (petroleum ether). Diastereoisomers could not be separated by this chromatographic method, however, this was not necessary for the further process anyway.

IR (KBr): ν$_{max}$ (cm$^{-1}$): 3221, 2915, 1715, 1137, 926, 833. MS (M$^+$): 329.

$^1$H-NMR: (300 MHz, TMS, CDCl$_3$).

A: δ: 0.05 (6H, s), 0.84 (9H, s), 1.16 (3H, d, J=6.3 Hz), 2.68 (2H, m), 2.98 (2H, m), 3.05 (1H, dd, J=2.25 Hz), 3.59 (1H, d, J=5.6 Hz), 4.09 (1H, dd, J=5.6 and 2.2 Hz), 4.20 (1H, m), 5.74 (1H, s);

B: δ: 0.05 (6H, s), 0.84 (9H, s), 1.21 (3H, d, J=6.3 Hz), 2.68 (2H, m), 2.98 (2H, m), 3.05 (1H, dd, J=2.2 Hz), 3.49 (1H, d, J=8.3 Hz); 3.81 (1H, dd, J=8.3 Hz, 2.2 Hz), 4.20 (1H, m), 6.25 (1H, s);

Ratio A:B=3:7.

EXAMPLE 8

(3S,4R)-3-((R)-(1-(tert-butyldimethylsilyl)oxy)ethyl)-4-((1RS)-2-oxocyclohexyl)-azetidine-2-one To a solution of cyclohexanone (6.2 ml; 60 mmole) in dichloromethane (60 ml) trimethylsilyl chloride (8.4 ml; 66 mmole) and 1,8-diazabicyclo[5.4.0]undec-7-ene (10.8 ml; 72 mmole) were added. The obtained mixture was stirred at the temperature of 40° C. for 2 hours. The solution was then diluted with hexane (40 ml) and then it was washed with saturated aqueous sodium hydrogencabonate solution (40 ml) and water (40 ml). The solution was dried with sodium sulfate, then the drying agent was filtered and the solvent was evaporated on rotavapor from the obtained filtrate. The crude trimethylsilyloxycyclohexene was used without purification in the next synthesis step in such a way that it was diluted with dichloromethane (15 ml) and the obtained solution was added to a solution of (3R,4R)-4-acetoxy-3-((R)-1-(tert-butyldimethylsilyloxy)ethyl)-azetidine-2 one (8.63 g; 30 mmole) in dichloromethane (10 ml). Then zinc iodide (9.57 g; 30 mmole) suspended in dichloromethane (15 ml) was added and the mixture was stirred at room temperature for 2 hours. To the mixture water (30 ml) and sodium hydrogencarbonate (2.55 g; 30 mmole) were added and it was stirred for 5 minutes. The phases were separated and the aqueous phase was washed with dichloromethane (2×10 ml). The combined organic phases were dried with sodium sulfate, then the drying agent was filtered off and the filtrate was evaporated to an oily residue. A crude product (65%) was obtained and further separated by column chromatography (silica gel, dichloromethane/ethyl acetate 5:1, (v/v)) into both diastereoisomers:

(3S,4R)-3-((R)-(1-(tert-butyldimethylsilyl)oxy)ethyl)-4-((1R)-2-oxocyclohexyl)-azetidine-2-one The title compound (2.94 g; 30%) in the form of white crystals with m.p. 108–110° C. (ethyl acetate) was obtained.

IR (KBr): ν$_{max}$ (cm$^{-1}$): 3283, 2948, 2857, 1755, 1716. MS (M$^+$): 325.

$^1$H-NMR (300 MHz, TMS, CDCl$_3$): δ: 0.03 (3H, s), 0.04 (3H, s), 0.83 (9H, s), 1.2 (3H, d, J=6.3 Hz), 1.5–2.16 (6H, m), 2.26–2.44 (2H, m), 2.48–2.58 (1H, m), 2.80–2.86 (1H, dd, J=5.1 Hz), 4.02–4.07 (1H, m), 4.12–4.20 (1H, dq, J=6.3 Hz), 5.82 (1H, rs).

(3S,4R)-3-((R)-(1-(tert-butyldimethylsilyl)oxy)ethyl)-4-((1S)-2-oxocyclohexyl)-azetidine-2-one The title compound (3.44 g; 35%) in the form of white crystals with m.p. 99–101° C. (ethyl acetate) was obtained.

IR (KBr): ν$_{max}$ (cm$^{-1}$): 3174, 2857, 2857, 1761, 1711. MS (M$^+$): 325.

$^1$H-NMR (300 MHz, TMS, CDCl$_3$): δ: 0.03 (3H, s), 0.05 (3H, s), 0.84 (9H, s), 1.19 (3H, d, J=6.2 Hz), 1.3–2.0 (6H, m), 2.12 (2H, m), 2.35 (1H, m), 2.66 (1H, dt, J=4.5 Hz and 1 Hz), 3.59 (1H, m), 4.13 (1H, dq, J=6.3 Hz), 6.10 (1H, rs).

EXAMPLE 9a

Allyl (8S,9R,10S)-10-((R)-(1-(tert-butyldimethylsilyl)oxy)ethyl)-11-oxo-1-azatricyclo-[7.2.0.018]undec-2-ene-2-carboxylate To a solution of (3S,4R)-3-((R)-(1-(tert-butyldimethylsilyl)-oxy)ethyl)-4-((1R)-2-oxocyclohexyl) azetidine-2-one (0.8 g; 2.46 mmole) prepared according to the process disclosed in Example 8 in dichloromethane (25 ml) triethylamine (0.99 ml; 0.72 g, 7.07 mmole) was added and the obtained mixture was cooled on an ice bath. To the obtained cooled solution allyl oxalyl chloride (0.56 ml; 0.77g, 5.23 mmole) was added drop by drop for 2 minutes and it was stirred at 0° C. for another 15 minutes. Then the solution was shaken with 5% aqueous hydrochloric acid solution (30 ml), with 5% aqueous sodium hydrogencarbonate solution (30 ml) and water (30 ml). The obtained solution was dried with sodium sulfate, then the drying agent was filtered off and the solvent was evaporated from the filtrate. Crude allyl (3S,4R)-2-oxo-3-((R)-(1-(tert-butyldimethylsilyl)oxy)ethyl)-4-((1R)-2-oxocyclohexyl) azetidine-1-yl)-glyoxylate (1.03 g (95%)) was obtained as a yellowish oil.

The obtained crude intermediate (1.03 g; 2.35 mole) was dissolved in toluene (40 ml), hydroquinone (25 g) was added and the obtained solution was heated to a temperature of 90° C. Under vigorous stirring triethylphosphite (2.04 ml; 1.95 g, 11.75 mmole) was added drop by drop to the solution for 5 minutes and it was stirred at the same temperature (90° C.) for another 2 hours. Then the reaction mixture was heated for 10 hours at the temperature of 120° C. Then the solvent was evaporated from the mixture and the oily residue was purified by column chromatography (silica gel, toluene/diethyl ether 4:1 (v/v)). The title compound (578 mg; 61%) was obtained in the form of a yellowish viscous oil.

IR (KBr): ν$_{max}$ (cm$^{-1}$): 2952, 2858, 1778, 1718. MS (M$^+$): 405.

¹H-NMR (300 MHz, TMS, CDCl₃): δ: 0.05 (6H, s), 0.85 (9H, s), 1.22 (3H, d, J=6 Hz), 1.2–2.2 (7H, m), 2.7–2.9 (1H, m), 3.16 (1H, dd, J=3.2 Hz and 6.8 Hz), 3.4–3.5 (1H, m), 4.08 (1H, dd, J=3.2 and 10.2 Hz), 4.18 (1H, dq, J=6.8 Hz and 6.0 Hz), 4.67 (1H, ddt, J=5.5 Hz, 13.6 Hz and 1.4 Hz), 4.80 (1H, ddt, J=5.5 Hz, 13.6 Hz and 1.4 Hz), 5.25 (1H, dq, J=10.4 Hz and 1.4 Hz), 5.43 (1H, dq, J=17.2 Hz and 1.4 Hz), 5.97 (1H, ddt, J=10.4 Hz, 17.2 Hz and 5.5 Hz).

EXAMPLE 9b

Allyl (8R,9R,10S)-10-((R)-(1-(tert-butyldimethylsilyl)oxy)ethyl)-11-oxo-1-azatricyclo-[7.2.0.0³,⁸]undec-2-ene-2-carboxylate The procedure was carried out in the same way as in Example 9a. (3S,4R)-3-((R)-(1-(tert-butyldimethylsilyl)oxy)ethyl)-4-((1S)-2-oxocyclohexyl)azetidine-2-one (1.5 g; 4.62 mmole) prepared according to the process disclosed in Example 8 was taken and the other reactants were used in the same molar ratios as in Example 9a. The title compound (1.09 g; 64%) was obtained in the form of a yellowish oil.

IR (film): $\nu_{max}$ (cm⁻¹): 2930, 2860, 1780, 1715. MS (M⁺): 405.

¹H-NMR (300 MHz, TMS, CDCl₃): δ: 0.05 (6H, s), 0.85 (9H, s), 1.27 (3H, d, J=6 Hz), 1.3–2.2 (7H, m), 2.8–2.9 (1H, m), 3.08 (1H, dd, J=2.8 and 7.6 Hz), 3.4–3.5 (1H, m), 3.60 (1H, dd, J=2.8 and 7.6 Hz), 4.15 (1H, dq, J=7.6 and 6.2 Hz), 4.66 (1H, J=5.5, 13.6 and 1.4 Hz), 4.80 (1H, ddt, J=5.5, 13.6 and 1.4 Hz), 5.25 (1H, dq, J=10.4 and 1.4 Hz), 5.43 (1H, dq, J=17.2 and 1.4 Hz), 5.97 (1H, ddt, J=10.4, 17.2 and 5.5 Hz).

EXAMPLE 10a

Allyl (8S,9S,10S)-10-((R)-(1-(tert-butyldimethylsilyl)oxy)ethyl)-11-oxo-1-aza-6-thiatricyclo[7.2.0.0³,⁸]undec-2-ene-2-carboxylate (3S,4S)-3-((R)-(1-(tert-butyldimethylsilyl)oxy)ethyl)-4-((3R)-4-oxotetrahydro-4H-thiopyrane-3-yl)azetidine-2-one (1.50 g; 4.37 mmole) prepared according to the process disclosed in Example 7a was dissolved in anhydrous dichloromethane (20 ml). The obtained solution was cooled to the temperature of −20° C. and allyl chloroglyoxylate (1.95 g; 13.1 mmole) was added thereto. Then a solution of ethyldiisopropylamine (3.38 g; 26.2 mmole) in anhydrous dichloromethane (5 ml) was added drop by drop to the mixture for 15 minutes under stirring at the temperature of −20° C. The obtained mixture was stirred at the same temperature for another 30 minutes and then for 1 hour at the temperature of 0° C. The obtained mixture was again cooled to the temperature of −20° C. and then a solution of allyl chloroglyoxylate (1.95 g) in anhydrous dichloromethane (5 ml) was added for 15 minutes drop by drop. The obtained solution was stirred. for 1 hour at the temperature of 0° C. and then for another hour at room temperature. The obtained mixture was quickly washed with 1M hydrochloric acid solution (20 ml), the aqueous phase was reextracted with dichloromethane (20 ml) and the combined organic phases were washed with 7% aqueous sodium hydrogencarbonate solution. The obtained solution was dried with magnesium sulfate, the drying agent was filtered off and the filtrate was evaporated to a residue which was a crude allyl (3S,4S)-3-((R)-(1-(tert-butyldimethylsilyl)oxy)ethyl)-4-((3R)-4-oxotetrahydrothiopyrane-3-yl)azetidine-2-one-1-glyoxylate.

The obtained residue after evaporation was dissolved in anhydrous toluene (250 ml) and hydroquinone (60 mg; 0.5 mmole) was added to the obtained solution. The mixture was heated in a nitrogen atmosphere to the reflux temperature, then a solution of triethyl phosphite (3.62 g; 21.8 mmole) in anhydrous toluene (20 ml) was slowly added drop by drop to the solution which was further heated in a nitrogen atmosphere at the reflux temperature for another 6 hours. The solvent was evaporated on rotavapor and the residue was purified by column chromatography (silica gel, diethyl ether/petroleum ether 1:5 (v/v)). The title compound (170 mg; 9%) was obtained in the form of an oil.

IR (film): $\nu_{max}$ (cm⁻¹): 1780, 1722, 1657, 1204, 1148, 1110, 982. MS (M⁺): 423.

¹H-NMR (300 MHz, TMS, CDCl₃): δ: 0.03 (6H, s), 0.84 (9H, s), 1.2 (3H, d, J=6.1 Hz), 2.34–2.72 (5H, m), 3.1–3.15 (2H, m), 3.78 (1H, dt, J=13 Hz, 3 Hz), 3.9-4.02 (1H, m), 4.1–4.2 (2H, m), 4.62–4.8 (2H, m), 5.26 (1H, dq, J=10.4 Hz, 1.4 Hz), 5.43 (1H, dq, J=17.2 Hz, 1.4 Hz), 5.95 (1H, ddt, J=10.4 Hz, 17.2 Hz, 5.4 Hz).

EXAMPLE 10b

Allyl (8R,9S,10S)-10-((R)-(1-(tert-butyldimethylsilyl)oxy)ethyl)-11-oxo-1-aza-6-thiatricyclo[7.2.0.0³,⁸]undec-2-ene-2-carboxylate The procedure was carried out in the same way as in Example 10a. (3S,4S)-3-((R)-(1-(tert-butyldimethylsilyl)oxy)ethyl)-4-((3S)-4-oxotetrahydro-4H-thiopyrane-3-yl)-azetidine-2-one (1.5 g; 4.37 mmole) prepared according to the process disclosed in Example 7a was taken and the other reactants were used in the same molar ratios as in Example 10a. The title compound (250 mg; 13.5%) was obtained in the form of an oil.

IR (film): $\nu_{max}$ (cm⁻¹): 1777, 1722, 1289, 1273, 1202, 1133, 984, 940. MS (M⁺): 423

¹H-NMR (300 MHz, TMS, CDCl₃): δ: 0.05 (6H, s), 0.85 (9H, s), 1.22 (3H, d, J=6.6 Hz), 2.3—2.9 (5H, m), 3.13 (1H, dd, J=7.0 Hz, 2.8 Hz), 3.2–3.35 (1H, m), 3.64 (1H, dd, J=7.3 Hz, 2.8 Hz), 3.74–3.86 (1H, m), 4.16 (1H, dq, J=7.0 Hz, 6.2 Hz), 4.6–4.8 (2H, m), 5.26 (1H, dq, J=10.4 Hz, 1.4 Hz), 5.39 (1H, dq, J=11.8 Hz, 1.4 Hz), 5.97 (1H, ddt, J=10.4 Hz, 11.8 Hz, 5.4 Hz).

EXAMPLE 10c

Allyl (8R,9S,10S)-10-((R)-(1-(tert-butyldimethylsilyl)oxy)ethyl)-11-oxo-1-aza-7-thia-tricyclo[7.2.0.0³,⁸]undec-2-ene-2-carboxylate The procedure was carried out in the same way as in Example 10a. (3S,4S)-3-((R)-(1-(tert-butyldimethylsilyl)oxy)ethyl)-4-((3S)-3-oxotetrahydrothiopyrane-2-yl)azetidine-2-one (1.5 g; 4.37 mmole) prepared according to the process disclosed in Example 7b was taken and the other reactants were used in the same molar ratios as in Example 10a. The title compound (125 mg; 6%) was obtained in the form of a yellow oil.

IR (film): $\nu_{max}$ (cm⁻¹): 2990, 1790, 1711. MS (M⁺): 423.

¹H-NMR: (300 MHz, TMS, CDCl₃): δ: 0.1 (6H, s), 0.85 (9H, s), 1.32 (6H, d), 1.8–2.7 (4H, m), 2.8–2.9 (1H, m), 3.22 (1H, dd, J=6.6 Hz, 3.1 Hz), 3.6–3.7 (1H, m), 3.75–3.83 (2H, m), 4.1–4.2 (1H, m), 4.75 (2H, dd, J=5.3 Hz, 1 Hz), 5.30 (1H, dd, J=10.4 Hz, 1.1 Hz), 5.38–5.46 (1H, m), 5.85–6.05 (1H, m).

EXAMPLE 10d

Allyl (7S,8S,9S)-9-((R)-(1-(tert-butyldimethylsilyl)oxy)ethyl)-10-oxo-1-aza-6-thiatricyclo[6.2.0.0³,⁷]dec-2-ene-2-carboxylate The procedure was carried out in the same way as in Example 10a up to the isolation of the title compound. The diastereoisomeric mixture (4.0 g; 12.1 mmole) of (3S,4S)-3-((R)-(1-(tert-butyldimethylsilyl)oxy)ethyl)-4-((2RS)-3-oxotetrahydrothiene-2-yl)-azetidine-2-one obtained according to the process disclosed in Example 7c was taken and the other reactants were used in the same molar ratios as in Example 10a. The title compound was isolated by column chromatography on silica gel (diethyl ether/petroleum ether 1:1 (v/v)). The title compound (0.81 g; 16%) was obtained in the form of white crystals with m.p. 88–94° C. (hexane).

IR (KBr): $v_{max}$ (cm$^{-1}$): 2940, 1717, 1257, 1095, 805. MS (M$^+$): 409.

$^1$H-NMR: (300 MHz, TMS, CDCl$_3$): δ: 0.06 (3H, s), 0.07 (3H, s), 0.88 (9H, s), 1.27 (3H, d), 2.55 (1H, m), 3.16 (1H, dd, J=2.8 and 6.4 Hz), 3.28 (3H, m), 4.17 (2H, m), 4.75 (3H, m), 5.35 (2H, m), 5.95 (1H, m).

EXAMPLE 11a

Allyl (8S,9R)-10-((E)-ethylidene)-11-oxo-1-azatricyclo-[7.2.0.0$^{3,8}$]undec-2-ene-2-carboxylate

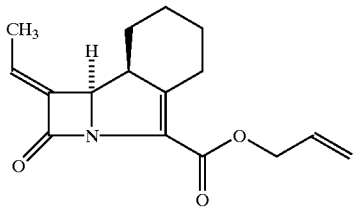

To a solution of allyl (8S,9R,10S)-10-((R)-(1-(tert-butyldimethylsilyl)oxy)ethyl)-11-oxo-1-azatricyclo-[7.2.0.0$^{3,8}$]undec-2-ene-2-carboxylate (405 mg;1 mmole) prepared according to the process disclosed in Example 9a in tetrahydrofuran (10 ml), 1M tetrabutylammonium fluoride solution (3 ml; 3 mmole) in tetrahydrofuran and acetic acid (0.23 ml; 4 mmole) were added. The obtained mixture was stirred for 2 hours at room temperature. Then the solution was shaken with saturated aqueous sodium hydrogencarbonate solution (10 ml) and the obtained mixture was extracted with ethyl acetate (3×15 ml). The organic phases were combined and dried with sodium sulfate, the drying agent was filtered off and the solvent was evaporated from the filtrate. (8S,9R,10S)-10-((R)-(1-hydroxyethyl)-11-oxo-1-azatricyclo-[7.2.0.0$^{3,8}$]undec-2-ene-2-carboxylate (267 mg; 92%) was obtained as a crude product in the form of a yellowish viscous oil.

IR (KBr): $v_{max}$ (cm$^{-1}$): 2935, 2858, 1770, 1716. MS (M$^+$): 291.

$^1$H-NMR (300 MHz, TMS, CDCl$_3$): δ: 1.33 (3H, d, J=6.2 Hz), 1.2–2.2 (7H, m), 1.74 (1H, d, J=4.8 Hz), 2.8–2.9 (1H, m), 3.21 (1H, dd, J=3 Hz and 6.6 Hz), 3.4–3.5 (1H, m), 4.18 (1H, dd, J=3 Hz, 10.2 Hz), 4.24 (1H, ddq, J=4.8 Hz), 6.6 Hz, 6.2 Hz), 4.68 (1H, ddt, J=5.5 Hz, 13.4 Hz, 1.5 Hz), 4.81 (1H, ddt, J=5.5 Hz, 13.4 Hz, 1.5 Hz), 5.26 (1H, dq, J=10.4 Hz, 1.5 Hz), 5.42 (1H, dq, J=17.2 Hz, 1.5 Hz), 5.98 (1H, ddt, J=10.4 Hz, 17.2 Hz and 5.5 Hz).

Allyl (8S,9R,10S)-10-((R)-(1-hydroxyethyl)-11-oxo-1-azatricyclo-[7.2.0.0$^{3,8}$]undec-2-ene-2-carboxylate (267 mg; 0.92 mmole) obtained according to the process as disclosed above was dissolved in dichloromethane (18 ml). The obtained solution was cooled on an ice bath and triphenylphosphine (239 mg; 0.92 mmole) and diethyl azodicarboxylate (0.14 ml; 0.92 mmole) were added thereto. The obtained solution was heated to room temperature and stirred for 15 minutes, then the solution was again cooled on an ice bath and triphenylphosphine (239 mg; 0.92 mmole) and diethyl azodicarboxylate (0.14 ml; 0.92 mmole) were added thereto. The obtained solution was again stirred at room temperature for 15 minutes, then the solvent was evaporated and the product was purified on a chromatographic column (petroleum ether/ethyl acetate 2:1). The title compound (180 mg; 72%) was obtained in the form of a slightly yellowish oil.

IR (KBr): $v_{max}$ (cm$^{-1}$): 2918, 2840, 1745, 1705. MS (M$^+$): 273.

$^1$H-NMR (300 MHz, TMS, CDCl$_3$): δ: 1.12–1.48 (4H, m), 1.80 (3H, dd, J=7.1 Hz, 1 Hz), 1.82–1.92 (2H, m), 1.99–2.11 (1H, td, J=13 and 4.4 Hz), 2.80–2.91 (1H, dddd, J=10.5 Hz, 5.1 Hz), 3.38–3.47 (1H, m), 4.63–4.83 (3H, m), 5.20–5.26 (1H, dddd, J=10.5 Hz, 1.5 Hz), 5.36–5.45 (1H, dddd, J=17.3 Hz, 1.5 Hz), 5.88–6.03 (1H, m), 6.41–6.50 (1H, dq, J=7.1 Hz, 1.7 Hz).

EXAMPLE 11b

Allyl (8R,9R)-10-((E)-ethylidene)-11-oxo-1-azatricyclo-[7.2.0.0$^{3,8}$]undec-2-ene-2-carboxylate

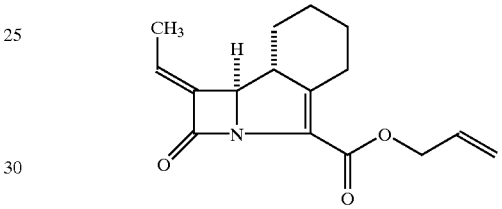

The procedure was carried out as in the first part of Example 11a. Allyl (8R,9S,10S)-10-((R)-(1-(tert-butyldimethylsilyl)oxy)ethyl)-11-oxo-1-aza-6-thiatricyclo [7.2.0.0$^{3,8}$]undec-2-ene-2-carboxylate (643 mg; 1.6 mmole) prepared according to the process disclosed in Example 10b was taken and the other reactants were used in the same molar ratios as in Example 11a. Crude allyl (8R,9R,10S)-10-((R)-(1-hydroxyethyl)-11-oxo-1-azatricyclo-[7.2.0.0$^{3,8}$]undec-2-ene-2-carboxylate (446 mg; 96.5%) was obtained in the form of a yellowish oil.

IR (KBr): $v_{max}$ (cm$^{-1}$): 2930, 2850, 1765, 1720. MS (M$^+$): 291.

$^1$H-NMR (300 MHz, TMS, CDCl$_3$): δ: 1.33 (3H, d, J=6.2 Hz), 1.2–2.3 (7H, m), 1.76 (1H, d, J=4.8 Hz), 2.8–3.0 (1H, m), 3.13 (1H, dd, 3=2.8 Hz, 6.6 Hz), 3.4–3.5 (1H, m), 3.71 (1H, dcl, J=2.8 Hz, 7.6 Hz), 4.22 (1H, ddq, J=4.8 Hz, 6.6 Hz, 6.2 Hz), 4.68 (1H, ddt, J=5.5 Hz, 13.4 Hz, 1.5 Hz), 4.81 (1H, ddt, J=5.5 Hz, 13.4 Hz, 1.5 Hz), 5.26 (1H, dq, J=10.4 Hz, 1.5 Hz), 5.42 (1H, dq, J=17.2 Hz, 1.5 Hz), 5.98 (1H, ddt, J=10.4 Hz, 17.2 Hz, 5.5 Hz).

The procedure was continued as in the second part of Example 11a. Crude allyl (8R,9R,10S)-10-((R)-(1-hydroxyethyl)-11-oxo-1-azatricyclo-[7.2.0.0$^{3,8}$]undec-2-ene-2-carboxylate (446 mg; 1.53 mmole) was used. A crude product was obtained which was purified on a chromatographic column (silica gel, petroleum ether/ethyl acetate 2:1 (v/v)) to obtain the title compound (333 mg; 76%) in the form of a slightly yellowish oil.

IR (KBr): $v_{max}$ (cm$^{-1}$): 2910, 2840, 1750, 1705. MS (M$^+$): 273.

$^1$H-NMR (300 MHz, TMS, CDCl$_3$): δ: 1.10–1.50 (4H, m), 1.82 (3H, dd, J=7.1 Hz, 1 Hz), 1.82–1.92 (2H, m), 1.99–2.11 (1H, td, J=13 Hz, 4.4 Hz), 2.80–2.91 (1H, dt,

J=10.5 Hz, 5.1 Hz), 3.40–3.46 (1H, m), 4.63–4.83 (3H, m), 5.20–5.26 (1H, dddd, J=10.5 Hz, 1.5 Hz), 5.36–5.45 (1H, dddd, J=17.3 Hz, 1.5 Hz), 5.88–6.03 (1H, m), 6.41–6.50 (1H, dq, J=7.1 Hz, 1.7 Hz).

EXAMPLE 11c

Allyl (8S,9R)-10-((E)-ethylidene)-11-oxo-1-aza-6-thiatricyclo-[7.2.0.0$^{3,8}$]undec-2-ene-2-carboxylate

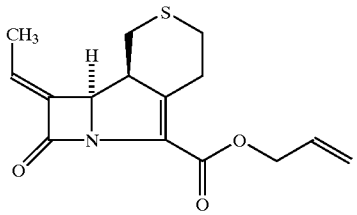

Up to the isolation the procedure was carried out in the same way as in Example 11a. Allyl (8S,9S,10S)-10-((R)-(1-(tert-butyldimethylsilyl)oxy)ethyl)-11-oxo-1-aza-6-thiatricyclo[7.2.0.0$^{3,8}$]undec-2-ene-2-carboxylate (424 mg) prepared according to the process disclosed in Example 10a was taken and the other reactants were used in the same molar ratios as in Example 11a. The crude product was purified by column chromatography (silica gel, diethyl ether/petroleum ether 2:1 (v/v)) to obtain the title compound (85 mg; 29%) in the form of a viscous oil.

IR (film): $v_{max}$ (cm$^{-1}$): 1760, 1717, 1373, 1266, 1182, 1146, 1097. MS (M$^+$): 291.

$^1$H-NMR (300 MHz, TMS, CDCl$_3$): δ: 1.86 (3H, dd, J=7.3 Hz, 0.98 Hz), 2.4–2.72 (5H, m), 3.25 (1H, ddt, J=5.4 Hz, 10.8 Hz, 0.98 Hz), 3.82 (1H, dt, J=13.2 Hz, 2.9 Hz), 4.67–4.86 (3H, m), 5.25–5.3 (2H, m), 5.44 (1H, dq, J=17.2 Hz, 1.4 Hz), 5.98 (1H, ddt, J=10.4 Hz, 17.2 Hz, 1.4 Hz), 6.55 (1H, dq, J=7.2 Hz, 1.8 Hz).

EXAMPLE 12

Allyl (8R,9S,10S)-10-((R)-(1-(methanesulfonyl)oxy)ethyl)-11-oxo-1-aza-6-thiatricyclo[7.2.0.0$^{3,8}$]undec-2-ene-2-carboxylate

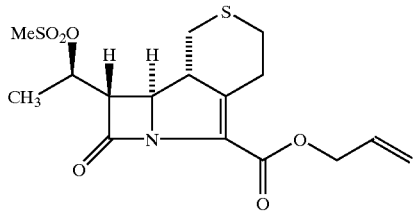

Allyl (8R,9S,10S)-10-((R)-(1-(tert-butyldimethylsilyl)oxy)ethyl)-11-oxo-1-aza-6-thiacyclo[7.2.0.0$^{3,8}$]undec-2-ene-2-carboxylate (652 mg; 154 mmole) obtained according to the process disclosed in Example 10b was dissolved in anhydrous tetrahydofuan 8 ml). To the obtained solution a mixture of 1M tetrabutylammonium mmole) was added. The obtained mixture was stirred for 24 hours at room temperature. Then ethyl acetate (36 ml) and water (18 ml) were added to the mixture. The obtained phases were separated and the obtained aqueous phase was reextracted with ethyl acetate (18 ml). The combined organic phases were washed with 7% aqueous sodium hydrogencarbonate solution and dried with magnesium sulfate. Then the drying agent was filtered off and the solvent was evaporated from the filtrate. The residue after evaporation was dissolved in anhydrous dichloromethane (40 ml) and to the solution at the temperature of 0° C. first triethyl amine (615 mg; 6.1 mmole) and then methanesulfonyl chloride (353 mg; 3.1 mmole) were added. The obtained mixture was stirred for another 30 minutes on an ice bath. The solvent was evaporated on rotavapor and the residue after evaporation was purified by fast-elution column chromatography (silica gel, diethyl ether/petroleum ether 3:1 (v/v)). The title compound (130 mg; 22%) was obtained in the form of a viscous oil.

IR (film): $v_{max}$ (cm$^{-1}$): 1771, 1716, 1316, 1173, 1145, 903. MS (M$^+$): 387.

$^1$H-NMR (300 MHz, TMS, CDCl$_3$): δ: 1.32 (3H, d, J=6.30 Hz), 1.56 (3H, d, J=6.36 Hz), 2.30–2.90 (5H, m), 3.10 (1H, dd, J=7.0 Hz, 2.8 Hz), 3.28–3.42 (1H, m), 3.64 (1H, dd, J=7.6 Hz, 2.8 Hz), 3.76–3.82 (1H, m), 4.26 (1H, dq, J=7.0 Hz, 6.2 Hz), 4.70–4.82 (2H, m), 5.26 (1H, dq, J=10.4 Hz, 1.4 Hz), 5.40 (1H, dq, J=17.2 Hz, 1.4 Hz), 5.96 (1H, ddt, J=10.4 Hz, 17.2 Hz, 5.4 Hz).

EXAMPLE 13

Allyl (8R,9R)-10-((E)-ethylidene)-11-oxo-1-aza-6-thiatricyclo-[7.2.0.0$^{3,8}$]undec-2-ene-2-carboxylate

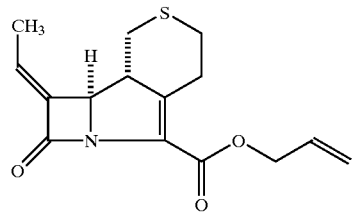

Allyl (8R,9S,10S)-10-((R)-(methanesulfonyl)oxy)ethyl)-11-oxo-1-aza-6-thia-tricyclo[7.2.0.0$^{3,8}$]undec-2-ene-2-carboxylate (55 mg; 0.14 mmole) obtained according to the process disclosed in Example 12 was dissolved in anhydrous dichloromethane (20 ml). The obtained mixture was cooled to the temperature of −20° C. and 1,8-diazabicyclo[5.4.0]undec-7-ene (21.4 mg; 0.14 mmole) was added. The obtained solution was stirred for 1 hour at the temperature of −20° C., then 2 hours at the temperature between −20° C. and 0° C. and for another hour at room temperature. Then the solvent was evaporated from the solution and the separated product was purified by column chromatography (silica gel, diethyl ether/petroleum ether 3:1 (v/v)). The title compound (30 mg; 72%) was obtained in the form of a viscous oil.

IR (film): $v_{max}$ (cm$^{-1}$): 1768, 1716, 1502, 1367, 1269, 1196, 1152, 871. MS (M$^+$): 291.

$^1$H-NMR (300 MHz, TMS, CDCl$_3$): δ: 1.83 (3H, dd, J3=0.74 Hz, 7.4 Hz), 2.29 (1H, ddt, J=5.12 Hz, 13.60 Hz, 3.16 Hz), 2.54–2.78 (3H, m), 2.90–2.98 (1H, m), 3.18–3.28 (1H, m), 3.82 (1H, dd, J=2.94 Hz, 14.98 Hz), 4.22–4.28 (1H, m), 4.66–4.84 (2H, m), 5.26 (1H, dq, J=10.4 Hz, 1.4 Hz), 5.42 (1H, dq, J=11.8 Hz, 1.4 Hz), 6.00 (1H, ddt, J=10.4 Hz, 11.8 Hz, 5.4 Hz), 6.38 (3H, dq, J=7.0 Hz, 1.4 Hz).

EXAMPLE 14

Allyl (8R,9R)-10-((E)-ethylidene)-11-oxo-1-aza-6-thiatricyclo-[7.2.0.0³,⁸]undec-2-ene-2-carboxylate

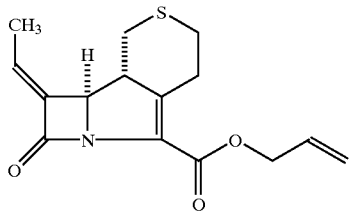

The procedure was carried out in the same way as in Example 12. Allyl (8R,9S,10S)-10-((R)-(1-(tert-butyldimethylsilyl)oxy)ethyl)-11-oxo-1-aza-6-thiatricyclo [7.2.0.0³,⁸]undec-2-ene-2-carboxylate (650 mg; 1.53 mmole) obtained according to the process disclosed in Example 10b was taken and the other reactants were used in the same molar ratios as in Example 12. The crude product was slowly eluted through a silica gel column with diethyl ether/petroleum ether mixture 3:1, whereat a spontaneous elimination of methanesulfonic acid and isolation of the title compound occured. The title compound (152 mg; 34%) was obtained and it was identical to the compound prepared according to the process disclosed in Example 13.

EXAMPLE 15a

Sodium (8S,9R)-10-((E)-ethylidene)-11-oxo-1-azatricyclo-[7.2.0.0³,⁸]undec-2-ene-2-carboxylate

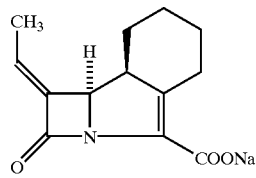

Allyl (8S,9R)-10-((E)-ethylidene)-11-oxo-1-azatricyclo-[7.2.0.0³,⁸]undec-2-ene-2-carboxylate (73 mg; 0.267 mmole) prepared according to the process disclosed in Example 11a was dissolved in a mixture (0.5 ml) of tetrahydrofuran/dichloromethane 1:1 (v/v). To the obtained mixture there were added first a solution of triphenylphosphine (24 mg; 0.08 mmole) and then a solution of sodium 2-ethylhexanoate (46.8 mg; 0.28 mmole) and tetrakis (triphenylphosphine)palladium(0) (32 mg; 0.024 mmole) (prepared according to the process disclosed in D. R.Coulson, Inorganic Synthesis 13, 121 (1972)) in a mixture (2 ml) of tetrahydrofuran/dichloromethane (1:1). The obtained solution was stirred for 30 minutes at room temperature. To the obtained mixture diethyl ether (4 ml) was added and it was cooled to the temperature of 0° C. The separated product was filtered off, washed with an anhydrous mixture of diethyl ether/tetrahydrofuran and dried in vacuo. The title compound (32 mg; 47%) was obtained in the form of brownish crystals and with m.p. 222–225° C. with decomposition (DMF-diethyl ether).

IR (Kbr): $v_{max}$ (cm$^{-1}$): 2933, 2858, 1740, 1592 MS (M-23)$^+$: 232.

$^1$H-NMR (300 MHz, TMS, DMSO-d$_6$): δ: 1.10–2.05 (7H, m), 1.77 (3H, d, J=7.1 Hz), 2.65–2.80 (1H, dt, J=10.3 Hz, 5.1 Hz), 3.54–3.64 (1H, m), 4.53–4.61 (1H, dd, J=10.3 Hz, 1.3 Hz), 6.21–6.30 (1H, dq, J=7.1 Hz, 1.3 Hz).

EXAMPLE 15b

Sodium (8R,9R)-10-((E)-ethylidene)-11-oxo-1-azatricyclo-[7.2.0.0³,⁸]undec-2-ene-2-carboxylate

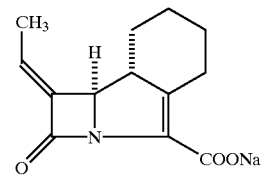

The procedure was carried out in the same way as in Example 15a. Allyl (8R,9R)-10-((E)-ethylidene)-11-oxo-1-azatricyclo-[7.2.0.0³,⁸]undec-2-ene-2-carboxylate (100 mg; 0.37 mmole) prepared according to the process disclosed in Example 11b was taken and the other reactants were used in the same molar ratios as in Example 15a. A crude product (48 mg; 51%) was obtained in the form of brownish crystals with m.p. 215–219° C. with decomposition (DMF—diethyl ether).

IR (KBr): $v_{max}$ (cm$^{-1}$): 2930, 2865, 1745, 1594 MS (M-23)$^+$: 232.

$^1$H-NMR (300 MHz, TMS, DMSO-d$_6$): δ: 1.05–2.10 (7H, m), 1.75 (3H, d, J=7.1 Hz), 2.65–2.80 (1H, dt, J=10.3 Hz, 5.1 Hz), 3.37–3.43 (1H, m), 4.53–4.61 (1H, dd, J=10.3 Hz, 1.3 Hz), 6.21–6.30 (1H, dq, J=7.1 Hz, 1.3 Hz).

EXAMPLE 15c

Sodium (8S,9R)-10-((E)-ethylidene)-11-oxo-1-aza-6-thiatrcyclo-[7.2.0.0³,⁸]undec-2-ene-2-carboxylate

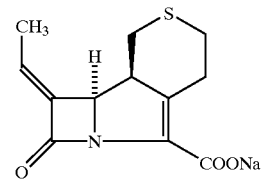

The procedure was carried out in the same way as in Example 15a. Allyl (8S,9R)-10-((E)-ethylidene)-11-oxo-1-aza-6-thiatricyclo-[7.2.0.0³,⁸]undec-2-ene-2-carboxylate (100 mg; 0.35 mmole) obtained according to the process disclosed in Example 11c was taken and the other reagents were used in the same molar ratios as in Example 15a. The crude product (78 mg; 83%) was obtained in the form of white crystals with m.p. 195–225° C. with decomposition (DMF—ether).

IR (KBr): $v_{max}$ (cm$^{-1}$): 3375, 1757, 1606, 1403, 1159, 1100, 975, 893. MS (M-23)$^+$: 250

$^1$H-NMR (300 MHz, TMS, DMSO-d$_6$): δ: 1.80 (3H, dd, J=7.08 Hz, 0.98 Hz), 2.34–2.64 (5H, m), 3.04 (1H, ddt, J=5.2 Hz, 10.6 Hz, 0.98 Hz), 3.98 (1H, dt, J=12.6 Hz), 4.66 (1H, d, J=10.0 Hz), 6.34 (1H, dq, J=7.08 Hz, 1.8 Hz).

EXAMPLE 15d

Sodium (8R,9R)-((E)-10-ethylidene)-11-oxo-1-aza-6-thiatricyclo-[7.2.0.0³,⁸]undec-2-ene-2-carboxylate

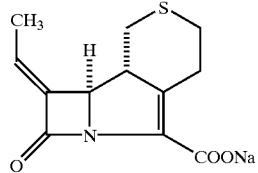

The procedure was carried out in the same way as in Example 15a. Allyl (8R,9R)-10-((E)-ethylidene)-11-oxo-1-aza-6-thiatricyclo-[7.2.0.0³,⁸]undec-2-ene-2-carboxylate (100 mg; 0.35 mmole) obtained according to the process disclosed in Example 14 was taken and the other reactants were used in the same molar ratios as in Example 15a. The crude product (38 mg; 40%) was obtained in the form of white crystals with m.p. 223–233° C. with decomposition (DMF—ether).

IR (KBr): $v_{max}$ (cm$^{-1}$): 3427, 1752, 1594, 1399, 1297, 1235, 1099. MS (M-23$^+$): 250.

$^1$H-NMR (300 MHz, TMSs, DMSO-d$_6$): δ: 1.76 (3H, d, J=7.4 Hz), 1.86–1.98 (1H, m), 2.41 (1H, dt, J=12.9 Hz, 2.92 Hz), 2.48–2.66 (2H, m), 2.70–3.20 (1H, m), 3.15–3.25 (1H, m), 3.96 (1H, dd, J=14.65 Hz, 2.8 Hz), 4.08–4.12 (1H, m), 6.18 (1H, dq, J=7.0 Hz, 1.5 Hz).

What is claimed is:

1. Ethylidene derivative of tricyclic carbapenems of formula I

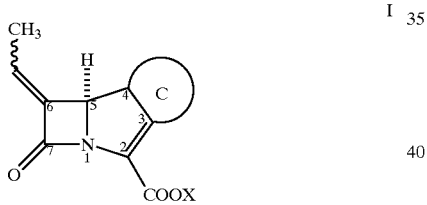

wherein ring C is a five-, six-, or seven-membered ring wherein said ring C is fused to said tricyclic carbapenem in the 3 and 4 positions of said carbapenem and wherein
 i. one or more carbon atoms of said ring C may be mono or disubstituted with substituents which may be the same or different wherein said substituents are selected from the group consisting of
  a) a hydrogen atom,
  b) a saturated alkyl chain with from 1 to 20 carbon atoms wherein said alkyl chain may be straight or branched in any position and wherein each said carbon atom of said alkyl chain may be mono or disubstituted with substituents wherein said substituents are selected from the group consisting of
   1) a halogen atom,
   2) hydroxy,
   3) (C$_1$–C$_4$)-alkyloxy,
   4) mercapto,
   5) (C$_1$–C$_4$)-alkylmercapto,
   6) (C$_1$–C$_4$)-alkanesulfonyl,
   7) amino,
   8) (C$_1$–C$_4$)-alkylamino,
   9) di-(C$_1$–C$_4$)-alkylamino,
   10) alkeneamino,
   11) guanidino,
   12) formamidino wherein said formamidino may be substituted with (C$_1$–C$_4$)-alkyl and wherein said substitution may comprise: unsubstituted, N$^1$-mono, N$^3$-mono, N$^1$,N$^3$-di, and N$^3$,N$^3$-di substitution,
   13) a first ring, wherein said first ring may be five- or six-membered and wherein said first ring may be aromatic or heteroaromatic, furyl, 2-pyridyl, phenyl
   14) (C$_1$–C$_4$)-alkyloxycarbonyl,
   15) cyano, and
   16) oxo,
  c) an unsaturated alkyl chain with from 2 to 20 carbon atoms wherein said unsaturated alkyl chain may be straight or branched in any position wherein said unsaturation may comprise double or triple bonds and wherein said unsaturation may occur in any position and wherein each said carbon atom of said alkyl chain may be mono or disubstituted with substituents wherein said substituents are selected from the group consisting of
   1) a halogen atom,
   2) hydroxy,
   3) (C$_1$–C$_4$)-alkyloxy,
   4) mercapto,
   5) (C$_1$–C$_4$)-alkylmercapto,
   6) (C$_1$–C$_4$)-alkanesulfonyl,
   7) amino,
   8) (C$_1$–C$_4$)-alkylamino,
   9) di-(C$_1$–C$_4$)-alkylamino,
   10) a second ring, wherein said second ring may be five- or six-membered and wherein said second ring may be aromatic or heteroaromatic, phenyl, furyl, 2-pyridyl,
   11) (C$_1$–C$_4$)-alkyloxycarbonyl,
   12) cyano, and
   13) oxo,
  d) a saturated or partly unsaturated cyclic radical wherein said radical has from 3 to 7 atoms and wherein said cyclic radical comprises atoms selected from the group consisting of carbon, oxygen, sulfur, and nitrogen and wherein each ring atom may be mono or distributed with substituents selected from the group consisting of halo, hydroxy, (C$_1$–C$_4$)-alkyloxy, mercapto, (C$_1$–C$_4$)-alkylmercapto, (C$_1$–C$_4$)-alkanesulfonyl, amino, (C$_1$–C$_4$)-alkylamino, di-(C$_1$–C$_4$)-alkylamino, (C$_1$–C$_4$)-alkyloxycarbonyl, cyano, and oxo,
  e) an aromatic or heteroaromatic five- or six-membered ring, phenyl, furyl, 2-pyridyl,
  f) a group selected from the group consisting of a hydroxy group, an unsubstituted, straight or branched (C$_1$–C$_{10}$)-alkyloxy, a straight or branched (C$_1$–C$_{10}$)-alkyloxy, which alkyl group may be mono or disubstituted with (C$_1$–C$_4$)-alkyl, an acyloxy, and a mono, di or tri-(C$_1$–C$_{10}$)-alkylsilyloxy;
  g) a group selected from the group consisting of mercapto, unsubstituted (C$_1$–C$_{10}$)-alkylmercapto, a (C$_1$–C$_{10}$)-alkylmercapto, which alkyl group may be mono or disubstituted with (C$_1$–C$_4$)-alkyl, and an acylmercapto;
  h) an amino, (C$_1$–C$_4$)-alkylamino and di-(C$_1$–C$_4$)-alkylamino, acetylamino, allyloxycarbonylamino, iminomethylamino, N-methylaminomethyleneamino, N,N-dimethylaminomethyleneamino, guanidino, cyanoguanidino, methylguanidino group, i) a halo atom,
j) an azido, nitro, cyano, $(C_1-C_4)$-alkyloxycarbonyl group,
k) a $(C_1-C_4)$-alkanesulfonyl group;

ii. one or more carbon atoms in the ring marked C may be substituted with a substituted or unsubstituted alkyl chain which is linked to the ring marked C via double bond in the form of >C*=CR$^1$R$^2$, and C* means a carbon atom in the ring marked C,=means an exocyclic double bond and substituents R$^1$ and R$^2$, which may be the same or different, may mean:
a) a hydrogen atom,
b) an unsubstituted saturated alkyl chain with 1 to 20 carbon atoms and the unsubstituted saturated alkyl chain may be straight or branched with double bonds in any position,
c) an unsubstituted unsaturated alkyl chain with 2 to 20 carbon atoms and the unsubstituted unsaturated alkyl chain may be straight or branched with double bonds or triple bonds,
d) an unsubstituted saturated or partly unsaturated cycloalkyl or heteroaryl with 3 to 7 members,
e) an aromatic or heteroaromatic five- or six-membered ring,
f) a substituted saturated or partly unsaturated alkyl chain or substituted three- to seven-membered carbocyclic ring whereby any carbon atom in the chain or in the ring may be mono or disubstituted with substituents selected from the group consisting of halo, hydroxy, $(C_1-C_4)$-alkyloxy, $(C_1-C_4)$-alkylmercapto, $(C_1-C_4)$-alkanesulfonyl, amino, $(C_1-C_4)$-alkylamino, di-$(C_1-C_4)$-alkylamino, $(C_1-C_4)$-alkyloxycarbonyl, cyano, and oxo,
g) a hydroxy, $(C_1-C_4)$-alkyloxy, acyloxy, mercapto, $(C_1-C_4)$-alkylmercapto, amino, $(C_1-C_4)$-alkylamino, di-$(C_1-C_4)$-alkylamino and acylamino group,
h) a nitro, cyano, $(C_1-C_4)$-alkyloxycarbonyl group;
and substituents R$^1$ and R$^2$ may also mean a joint alkylene chain $(CH_2)_n$ (n=2 to 7) closed to a ring and any methylene (—CH$_2$—) member may be replaced by an oxa (—O—), thia (—S—), imino (—NH—) or $(C_1-C_4)$-alkylimino group;

iii. one or more carbon atoms in the ring marked C may be substituted with a hetero atom via double bond;

iv. one or more of the carbon atoms in the ring marked C may be disubstituted with substituents closed to a ring to obtain a spiro compound and in said spiro ring one or more ring members may be oxygen, sulfur, or nitrogen atoms;

v. one or more carbon atoms in the ring marked C may be replaced by an oxygen atom;

vi. one or more carbon atoms in the ring marked C may be replaced with a sulfur atom which may be mono or dioxidized;

vii. one or more of the non-fused carbon atoms in the ring marked C may be replaced with a nitrogen atom which may be substituted in the form of >N*—R$^3$ and N* means a nitrogen atom in the ring marked C and R$^3$ may mean:
a) a saturated alkyl chain with 1 to 20 carbon atoms and an unsubstituted saturated chain with 1 to 20 carbon atoms may be straight or branched in any position and each chain member may be once or several times substituted with substituents such as halo, hydroxy, $(C_1-C_4)$-alkyloxy, $(C_1-C_4)$-alkylmercapto, $(C_1-C_4)$- alkanesulfonyl, amino, $(C_1-C_4)$-alkylamino, di-$(C_1-C_4)$-alkylamino, aromatic or heteroaromatic five- or six-membered ring, $(C_1-C_4)$-alkyloxycarbonyl, cyano, oxo, imino,
b) an substituted unsaturated alkyl chain with 2 to 20 carbon atoms and this unsubstituted unsaturated alkyl chain may be straight with double bonds or triple bonds or branched in any position with double or triple bonds,
c) an unsubstituted saturated or partly unsaturated cycloalkyl or heteroaryl radical with 3 to 7 members,
d) an unsubstituted aromatic or heteroaromatic five- or six-membered ring,
e) cyano, $(C_1-C_4)$-alkyloxycarbonyl, aminocarbonyl, $(C_1-C_4)$-alkylaminocarbonyl, $(C_1-C_4)$-alkanesulfonyl;

and wherein X may mean:
i. a hydrogen atom,
ii. an alkali metal,
iii. an alkali earth metal,
iv. a protonated form of a nitrogenous base,
v. an ammonium ion substituted with four $(C_1-C_{20})$-alkyl groups,
vi. a radical R$^4$ which is:
selected from the group consisting of $(C_1-C_{20})$-alkyl, $(C_2-C_{20})$-alkenyl, substituted alkyl, $(C_1-C_4)$-alkoxyalkyl, silyl, and phthalidyl;
b) a radical which is presented in the following form

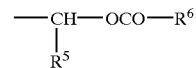

wherein
R$^5$ represents hydrogen, lower alkyl with 1 to 4 carbon atoms,
R$^6$ represents hydrogen, alkyl, cycloalkyl, alkoxy, cycloalkoxy, cycloalkylalkyl, alkenyloxy, phenyl.

2. Ethylidene derivative of tricyclic carbapenems of the formula I

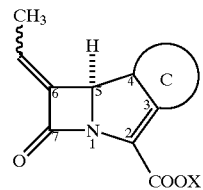

wherein the ring marked C and X have the meanings as given in claim 1, in the form of pure diastereoisomers.

3. Ethylidene derivative of tricyclic carbapenems of the formula I

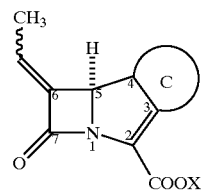

wherein the ring marked C and X have the meanings as given in claim 1, in the form of pure geometric isomers.

4. The derivative of claim 1 being (8S,9R)-10-((E)-ethylidene)-11-oxo-1-azatricyclo undec-2-ene-2-carboxylic acid, a pharmaceutically acceptable salt or ester thereof.

5. The derivative of claim 1 being (8R,9R)-10-((E)-ethylidene)-11-oxo-1-azatricyclo undec-2-ene-2-carboxylic acid, a pharmaceutically acceptable salt or ester thereof.

6. The derivative of claim 1 being (8S,9R)-10-((E)-ethylidene)-11-oxo-1-aza-6-thiatricyclo undec-2-ene-2-carboxylic acid, a pharmaceutically acceptable salt or ester thereof.

7. The derivative of claim 1 being (8R,9R)-10-((E)-ethylidene)-11-oxo-1-aza-6-thiatricyclo undec-2-ene-2-carboxylic acid, a pharmaceutically acceptable salt or ester thereof.

8. The derivative of claim 1 being (4S,8S,9R)-4-methoxy-10-((E)-ethylidene)-11-oxo-1-azatricyclo undec-2-ene-2-carboxylic acid, a pharmaceutically acceptable salt or ester thereof.

9. The derivative of claim 1 being (4R,8R,9R)-4-methoxy-10-((E)-ethylidene)-11-oxo-1-azatricyclo undec-2-ene-2-carboxylic acid, a pharmaceutically acceptable salt or ester thereof.

10. The derivative of claim 1 being (4S,8S,9R)-4-methoxymethyl-10-((E)-ethylidene)-11-oxo-1-azatricyclo undec-2-ene-2-carboxylic acid, a pharmaceutically acceptable salt or ester thereof.

11. The derivative of claim 1 being (4R,8R,9R)-4-methoxymethyl-10-((E)-ethylidene)-11-oxo-1-azatricyclo undec-2-ene-2-carboxylic acid, a pharmaceutically acceptable salt or ester thereof.

12. A process for the preparation of ethylidene derivative of tricyclic carbapenems of the formula I

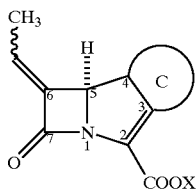

wherein the ring marked C and X have the meanings as in claim 1, wherein i. a compound of the formula II

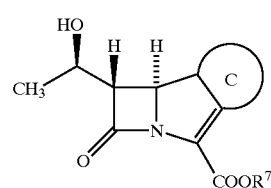

wherein $R^7$ is an ester protective group selected from the group consisting of alkyl, benzyl, 4-nitrobenyl, and tert-butyl and the ring marked C has the meaning as in claim 1, is at a temperature from −78° C. to the reflux temperature reacted with the corresponding reactive acid derivative in the presence of a base in an inert organic solvent or with the acid $R^8OH$ wherein $R^8$ has the below meaning, to yield a compound of the formula III

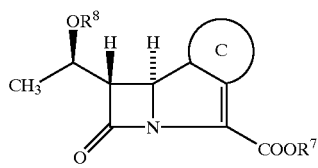

wherein $R^7$ and the ring marked C have the above meanings and $R^8$ may be
- a radical form of an aliphatic carboxylic acid having 1–10 carbons,
- a radical form of an aliphatic carboxylic halo acid having 1–10 carbons,
- an alkanesulfonyl radical, a haloalkanesulfonyl radical,
- an arenesulfonyl radical,
- a heteroarenesulfonyl radical;

ii. a compound of the formula III

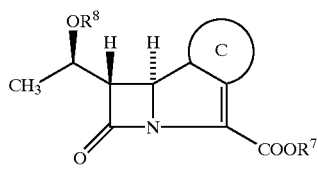

wherein $R^7$, $R^8$ and the ring marked C have the above meanings, is by base-catalyzed elimination at a temperature from −78° C. to the reflux temperature of the solvent in an inert organic solvent converted to a compound of the formula IV

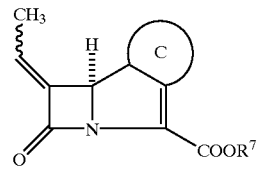

wherein $R^7$ and the ring marked C have the above meanings;

iii. a compound of the formula IV

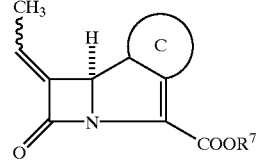

wherein $R^7$ and the ring marked C have the above meanings, is where appropriate, according to the usual methods for elimination of a protective group, converted to a compound of the formula I

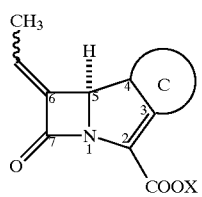

wherein the ring marked C and X have the meanings as in claim 1.

13. A process for the preparation of ethylidene derivative of tricyclic carbapenems of the Formula I

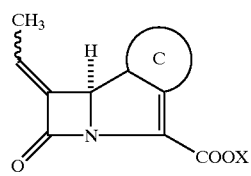

wherein the ring marked C and X have the meanings as in claim 1 wherein i. a compound of the formula II

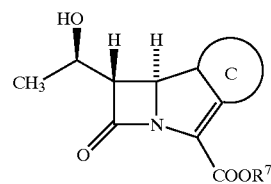

wherein R means an ester protective group selected from the group consisting of alkyl, benayl, 4-nitrobenzyl, and tert butyl and the ring marked C has the meaning as in claim 1, is, at a temperature from −78° C. to the reflux temperature of the solvent, reacted in an inert organic solvent with diazacarboxylates in the presence of phosphine to a compound of the formula IV

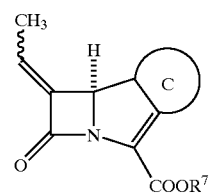

wherein $R^7$ and the ring marked C have the above meanings;

ii. a compound of the formula IV

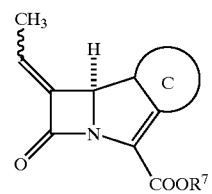

wherein $R^7$ and the ring marked C have the above meanings, is reacted according to the usual methods for elimination of a protective group to a compound of the formula I.

14. A pharmaceutical formulation comprising a therapeutically effective amount of an ethylidene derivative, according to claim 1, of tricyclic carbapenems of the formula I in the form of an acid, a pharmaceutically acceptable salt or ester as an active ingredient as well as usual pharmaceutically acceptable carriers and auxiliary substances.

15. A pharmaceutical formulation comprising a therapeutically effective amount of an ethylidene derivative, according to claim 1, of tricyclic carbapenems of the formula I in the form of an acid, a pharmaceutically acceptable salt or ester and a therapeutically effective amount of a β-lactam antibiotic as an active ingredient as well as usual pharmaceutically acceptable carriers and auxiliary substances.

16. A method for achieving an antibacterial effect in a human or a veterinary patient comprising administering a pharmaceutical formulation comprising a therapeutically effective amount of an ethylidene derivative of tricyclic carbapenems of formula I, according to claim 1, wherein said ethylidene derivative of tricyclic carbapenems comprises a pharmaceutically acceptable acid, salt or ester.

17. A method for inhibiting the catalytic activity of the enzyme β-lactamase in a human or a veterinary patient comprising administering a pharmaceutical formulation comprising a therapeutically effective amount of an ethylidene derivative of tricyclic carbapenems of formula I, according to claim 1, wherein said ethylidene derivative of tricyclic carbapenems is in the form of a pharmaceutically acceptable acid, salt or ester.

\* \* \* \* \*